US008998935B2

(12) United States Patent
Hart

(10) Patent No.: US 8,998,935 B2
(45) Date of Patent: Apr. 7, 2015

(54) SURGICAL STAPLE-CLIP AND APPLIER

(75) Inventor: Charles C Hart, Summerville, SC (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 888 days.

(21) Appl. No.: 12/200,582

(22) Filed: Aug. 28, 2008

(65) Prior Publication Data
US 2008/0319456 A1 Dec. 25, 2008

Related U.S. Application Data

(62) Division of application No. 10/533,398, filed as application No. PCT/US03/40318 on Dec. 16, 2003, now abandoned.

(60) Provisional application No. 60/434,344, filed on Dec. 17, 2002.

(51) Int. Cl.
A61B 17/08 (2006.01)
A61B 17/064 (2006.01)
(Continued)

(52) U.S. Cl.
CPC ......... *A61B 17/0644* (2013.01); *A61B 17/0643* (2013.01); *A61B 17/122* (2013.01);
(Continued)

(58) Field of Classification Search
USPC ......... 606/158, 139, 142, 143, 151, 157, 213, 606/215, 232
See application file for complete search history.

(56) References Cited

U.S. PATENT DOCUMENTS 3,137,027 A 6/1964 Birkle
3,166,072 A 1/1965 Sullivan, Jr.
(Continued)

FOREIGN PATENT DOCUMENTS

FR 2598905 5/1986
GB 807721 1/1959
GB 972731 10/1964

*Primary Examiner* — Gregory Anderson
(74) *Attorney, Agent, or Firm* — John F. Heal

(57) ABSTRACT

A surgical staple-clip including a clip component and a securing member is used in a wide range of surgical procedures. The staple-clip may be introduced to a surgical site in an un-assembled condition through a small port or trocar. An applier for the staple-clip comprising a pair of opposed jaw-like channels is provided to position and apply the clip component and the securing member. The clip component is positioned around a target tissue and is compressed or clamped upon the tissue using only the force required for a specific surgical procedure such as occlusion, ligation or fixation. When the clip component is properly applied, the securing member is urged forward and over the clip component to secure the staple-clip. The clip component may include traction enhancement features such as surface interruptions, bumps, valleys and ridges. With the staple-clip of the invention, the force required to constrict or occlude the tissue is separate from the force required to secure and maintain the staple-clip in position and, as a result, the body tissue is not over-compressed and nourishment to the body tissue is maintained. Other aspects of the invention include thumb actuated clip appliers for use in hand assisted laparoscopy (HAL) In one embodiment, a clip applier includes a handle and a thumb actuated mechanism that is used to slidably release clips onto a body tissue or vessel by sliding the thumb actuated mechanism forward and backward using only one hand. In another aspect of the invention, a two-stage clip is disclosed having a clip component and a staple component for securing the clip after it has been properly positioned.

21 Claims, 25 Drawing Sheets

(51) Int. Cl.
*A61B 17/122* (2006.01)
*A61B 17/068* (2006.01)
*A61B 17/128* (2006.01)
*A61B 17/00* (2006.01)

(52) U.S. Cl.
CPC .......... *A61B 17/068* (2013.01); *A61B 17/0682* (2013.01); *A61B 17/1285* (2013.01); *A61B 2017/00858* (2013.01); *A61B 2017/0641* (2013.01); *A61B 2017/0649* (2013.01); *A61B 2017/1225* (2013.01)

(56) References Cited

U.S. PATENT DOCUMENTS

| | | |
|---|---|---|
| 3,214,810 A | 11/1965 | Mathison |
| 3,254,650 A | 6/1966 | Collito |
| 3,326,217 A * | 6/1967 | Kerr .............................. 606/158 |
| 3,867,944 A | 2/1975 | Samuels |
| 3,950,829 A | 4/1976 | Cohen |
| 4,188,953 A | 2/1980 | Klieman et al. |
| 4,648,401 A | 3/1987 | Mattson |
| 4,784,137 A | 11/1988 | Kulik et al. |
| 4,924,864 A | 5/1990 | Danzig |
| 5,245,730 A | 9/1993 | Martin |
| 5,282,811 A | 2/1994 | Booker et al. |
| 5,358,510 A | 10/1994 | Luscombe et al. |
| 5,366,458 A | 11/1994 | Korthoff et al. |
| 5,411,481 A | 5/1995 | Allen et al. |
| 5,569,274 A * | 10/1996 | Rapacki et al. ................ 606/158 |
| 5,620,452 A | 4/1997 | Yoon |
| 5,713,912 A | 2/1998 | Porter |
| 5,843,098 A | 12/1998 | Allen et al. |
| 5,843,101 A * | 12/1998 | Fry ................................ 606/157 |
| 6,007,552 A | 12/1999 | Fogarty et al. |
| 6,139,555 A | 10/2000 | Hart et al. |
| 6,258,105 B1 | 7/2001 | Hart et al. |

\* cited by examiner

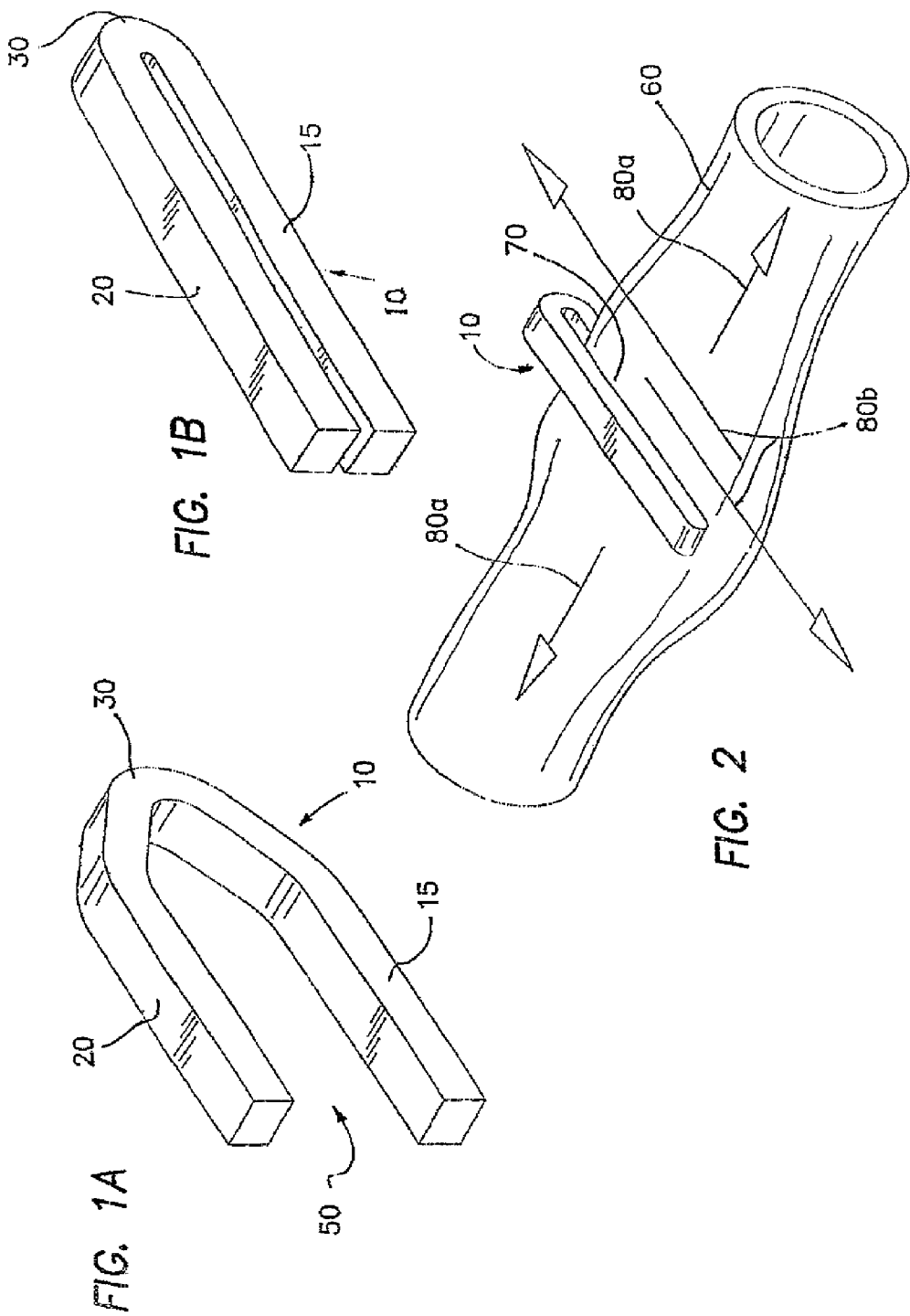

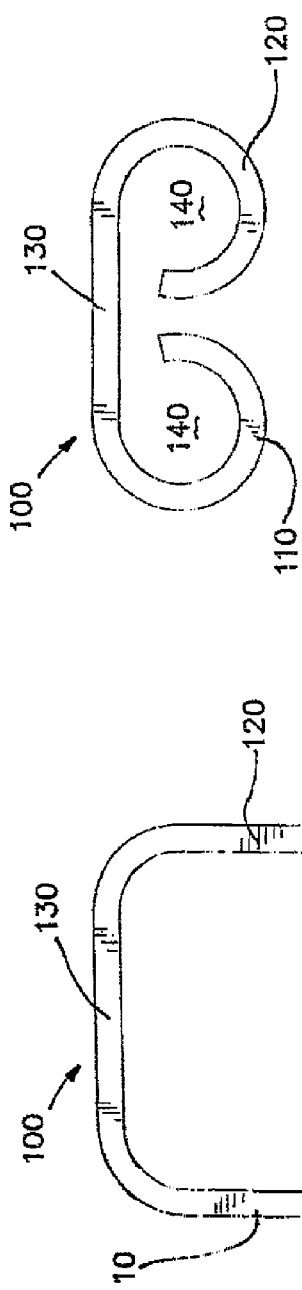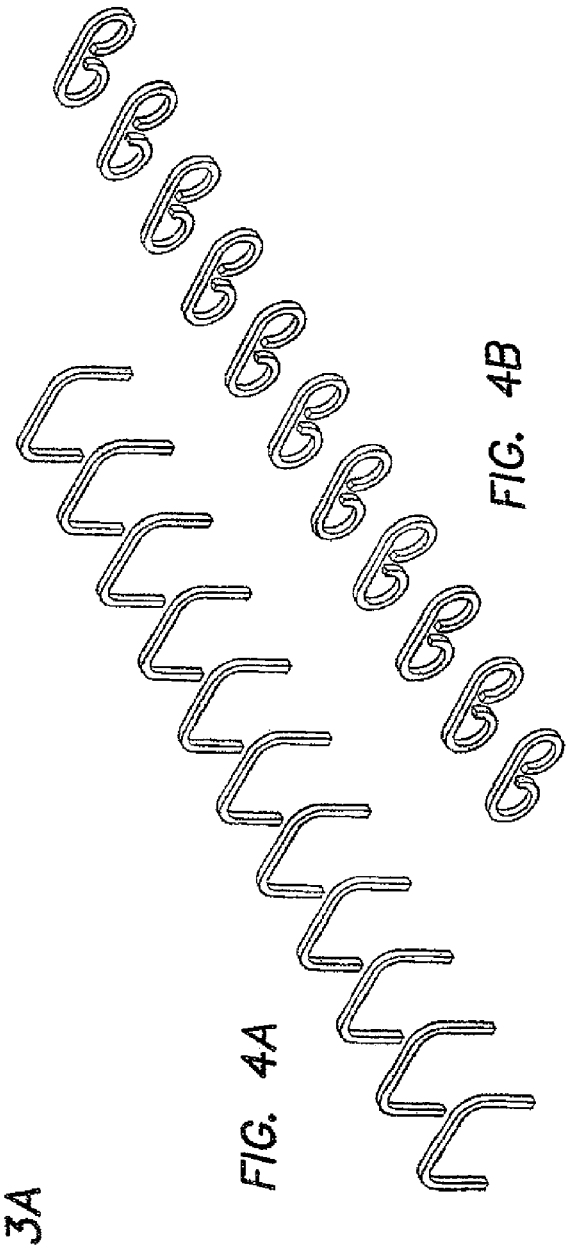

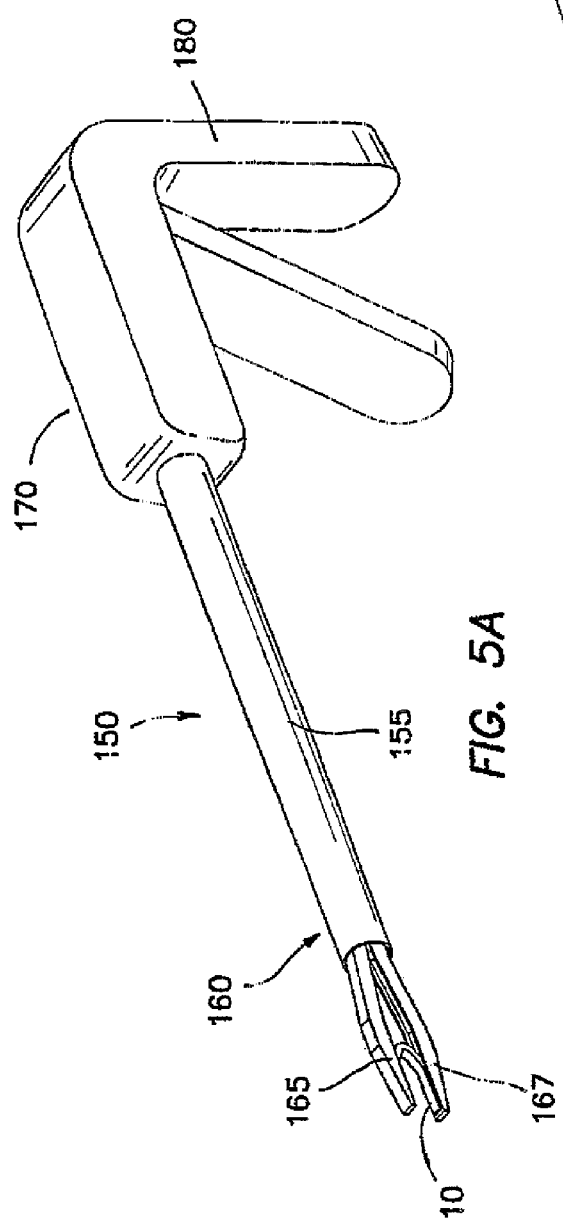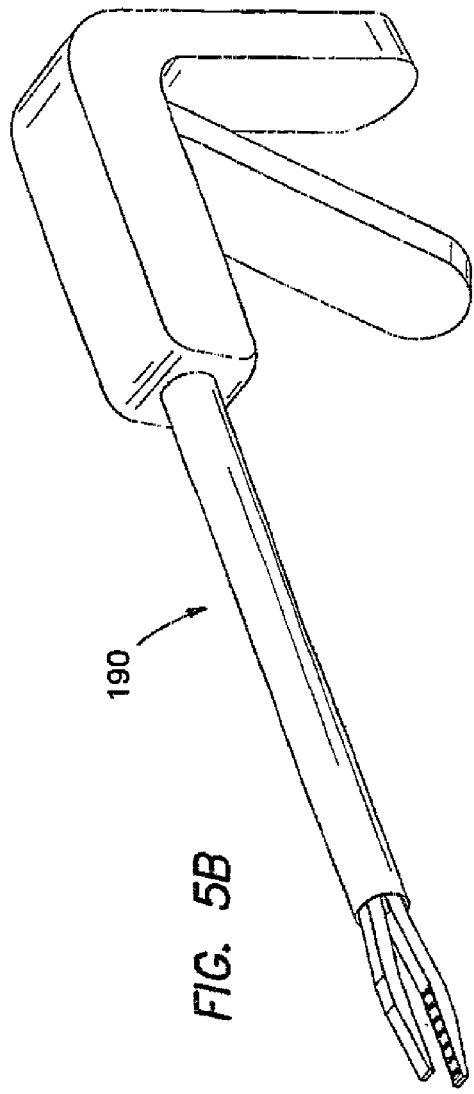

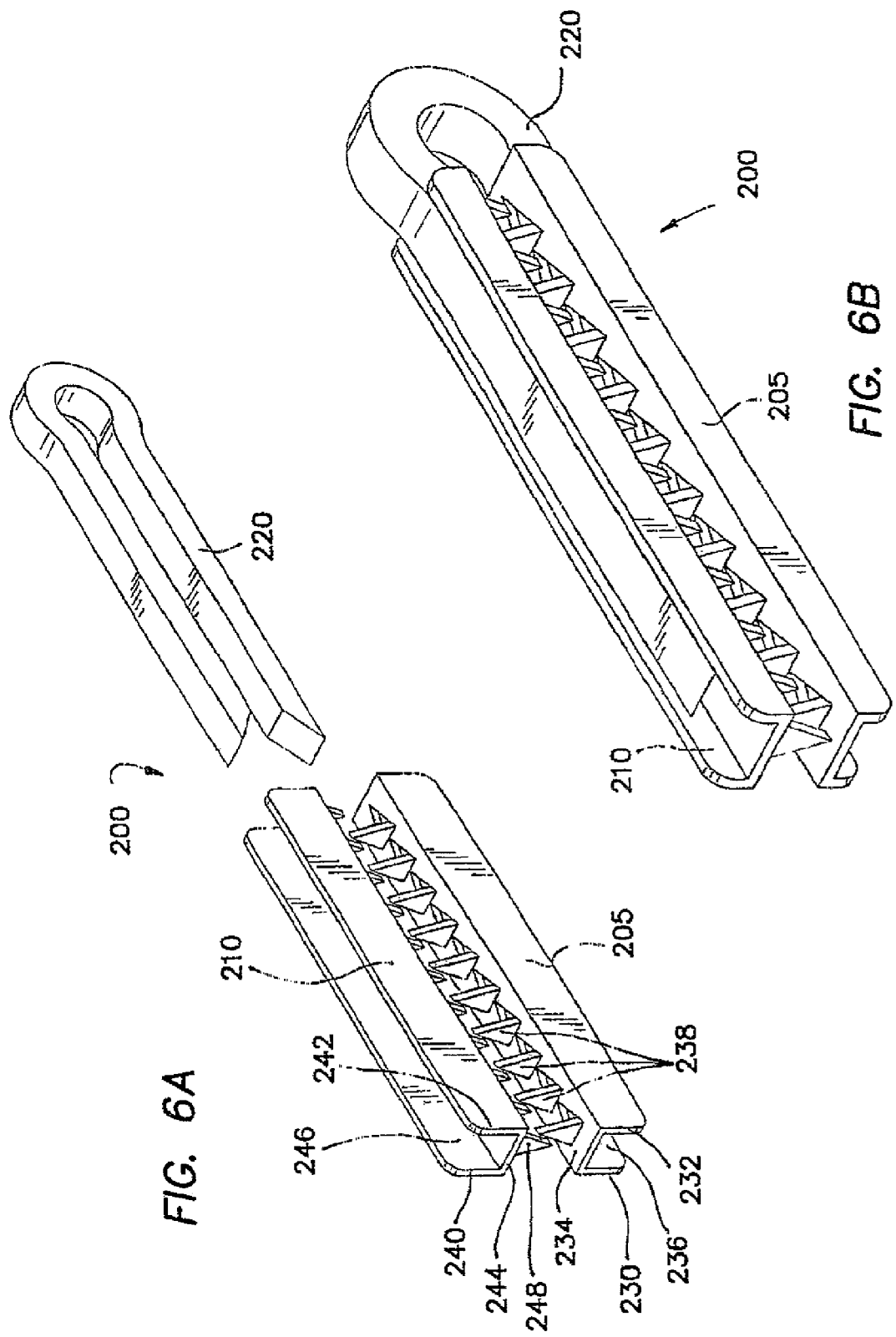

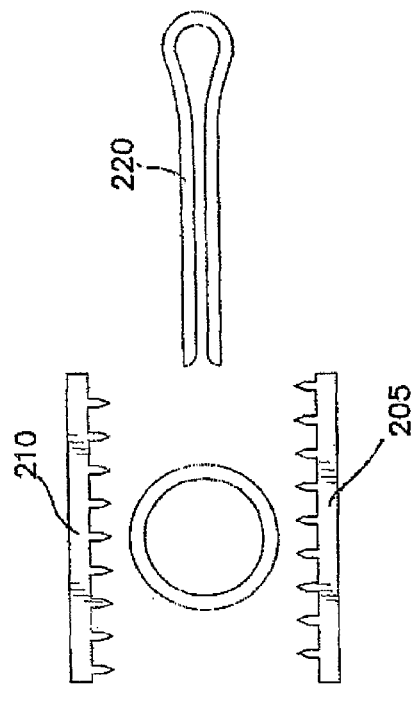
FIG. 11A
FIG. 11B
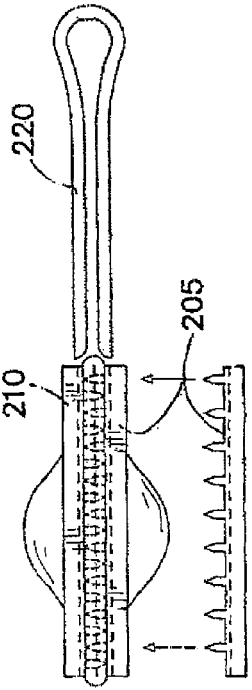
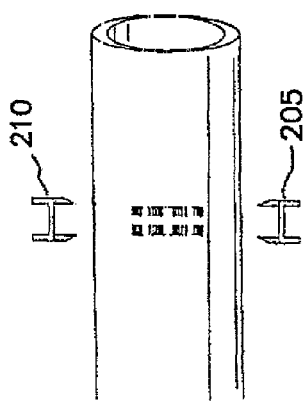
FIG. 11C
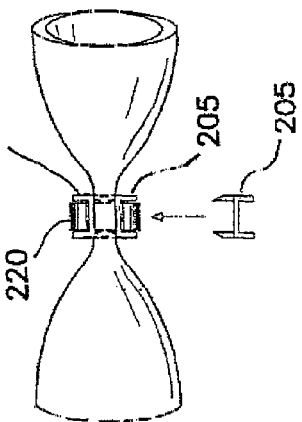
FIG. 11D

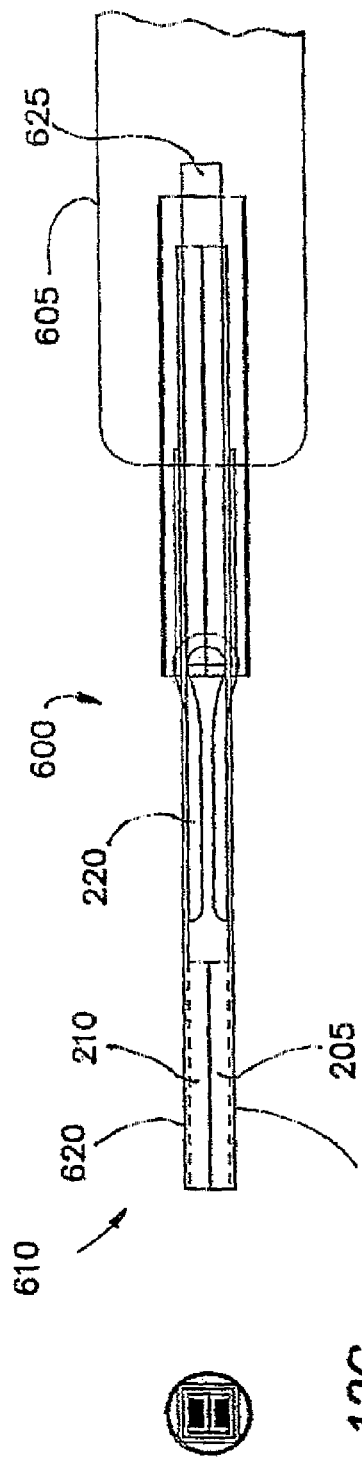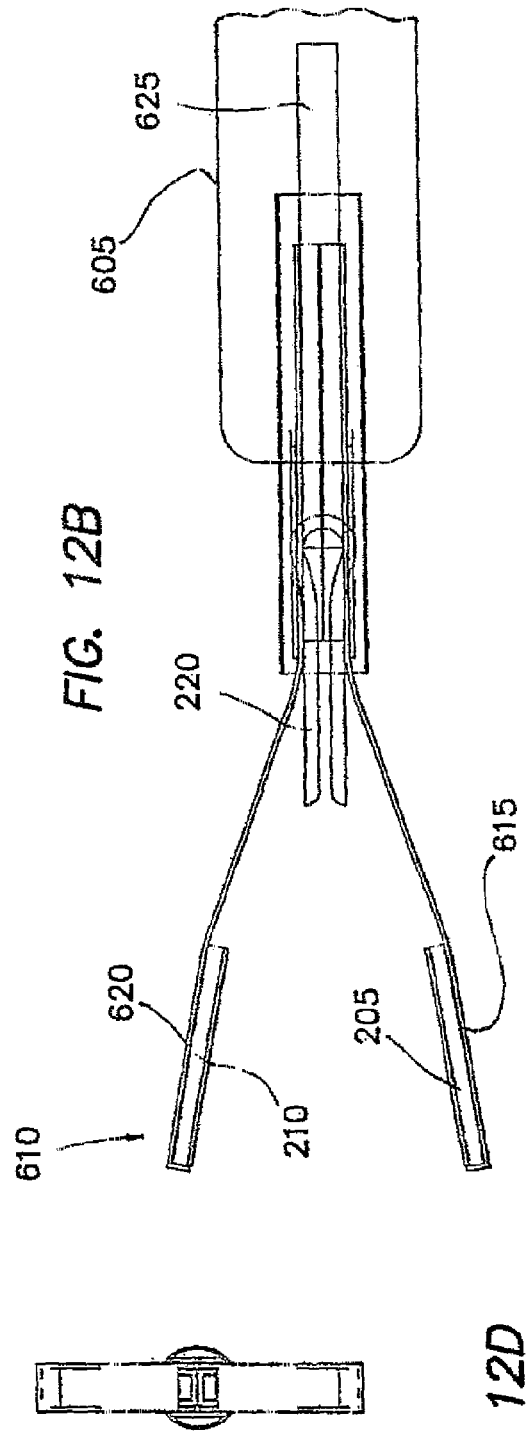

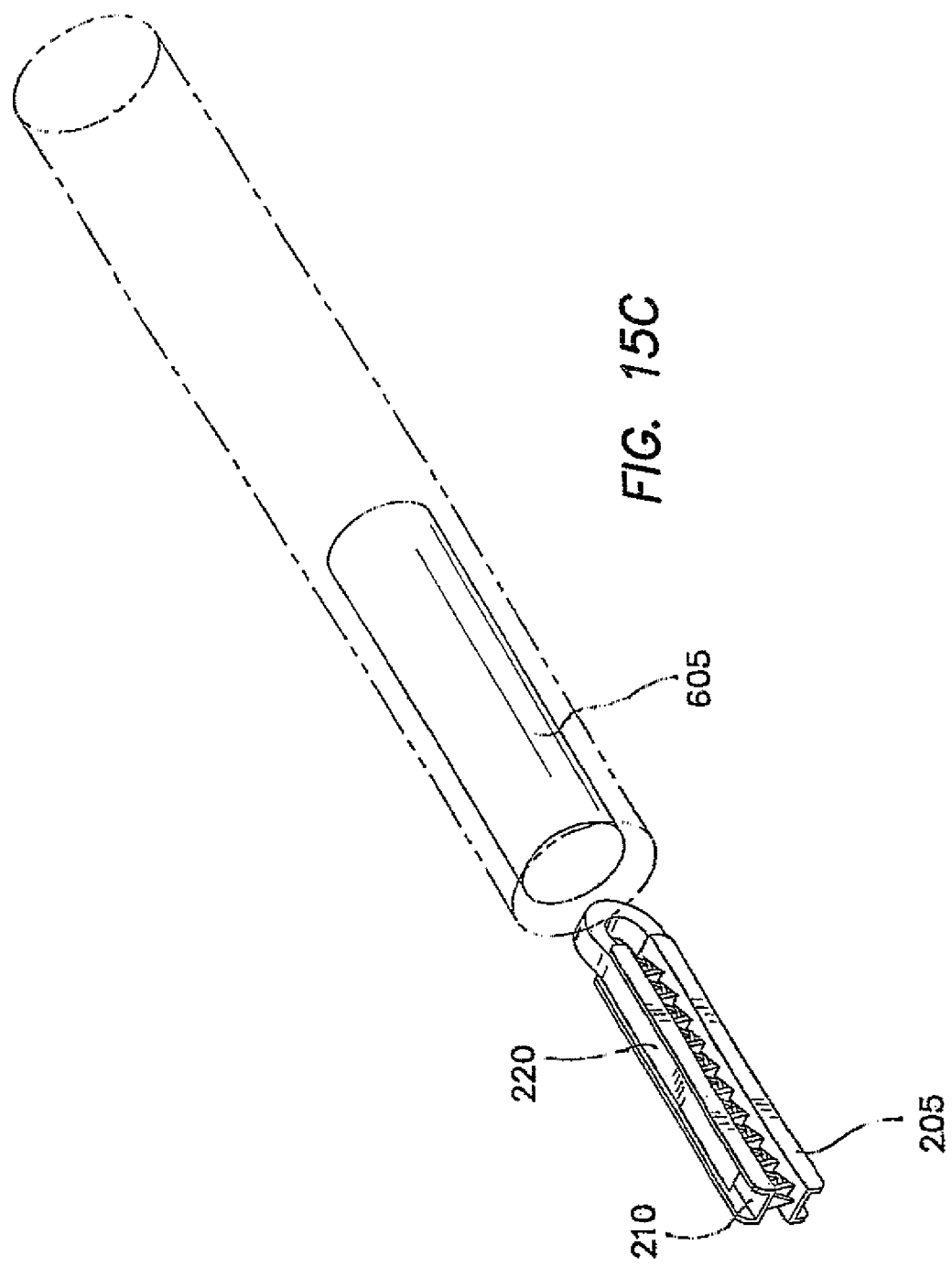

SURGICAL STAPLE-CLIP AND APPLIER

CROSS-REFERENCE TO RELATED APPLICATIONS

This application is a divisional of U.S. patent application Ser. No. 10/533,398, filed on Apr. 30, 2005, currently pending, which is a 371 international application of PCT Application No. PCT/US03/040318, filed on Dec. 16, 2003, which claims benefit of U.S. Provisional Patent Application No. 60/434,344, filed on Dec. 17, 2002, the disclosures of which are hereby incorporated by reference as if set forth in full herein.

BACKGROUND OF THE INVENTION

1. Field of the Invention

This invention generally relates to medical devices and, more specifically, to a staple-clip and applier adapted for use in surgical procedures 2. Discussion of the Prior Art Clips and staples are widely used in many surgical procedures such as occlusion, ligation and fixation of various body tissues and vessels. Clips are generally U-shaped, open-ended wires that are positioned around a target tissue and clamped together to constrict or occlude the tissue. A clip applier is typically used for applying the clips Clip appliers can be configured for applying a single clip or multiple clips in both open and minimally invasive or laparoscopic surgeries. The individual clips are provided in a loading cartridge or rack of a clip applier. With minimally invasive surgery, a clip applier must be able to deliver clips through a small access port or trocar having a diameter of about 10 mm to 12 mm. Accordingly, the size of a deliverable laparoscopic clip must be smaller than the inside diameter of the trocar through which it is introduced. Typically, a 12 mm clip applier is capable of delivering a clip that is no longer than 7-8 mm. It is not uncommon for laparoscopic surgeons to discover that even the largest clip available is undersized for a particular surgical procedure Moreover, clips will occasionally move about or slip off the tissue to which they have been applied. In some cases, a surgeon may apply an excessive compressive force to the clip and tissue to minimize movement or slippage of the clip. This excessive compression may cause necrosis of tissue since nutrition to the tissue is interrupted or eliminated.

Staples are also widely used in many surgical procedures to constrict or occlude a body tissue or vessel. A surgical staple typically includes a pair of penetrating legs connected by a base portion. Surgical staples are applied using a stapler, which compresses the penetrating legs as the legs advance through the body tissue and are bent against an opposing jaw of the stapler to secure the staple to the body tissue. A feature of the staple is it defines open portions that provide nourishment to the tissue even when the staple is bent. Surgical staples have proved to be effective, however, the staplers used for applying the staples are often bulky and require a very strong closing or compressing force, which is not ideal for minimally invasive or laparoscopic surgeries. As such, it is desirable to find a staple/clip providing good traction to prevent movement and slippage while requiring only a force to close or compress the staple/clip. Specifically, it is desirable to have a staple/clip where the force required to constrict or occlude a body tissue is separate from the force required to secure and maintain the device in position. The staple-clip would provide good traction while maintain proper nourishment to the body tissue. It is advantageous to use the staple/clip, for example, to secure the renal vessel in donor nephrectomy.

SUMMARY OF THE INVENTION

The present invention is directed to a surgical staple-clip for use in a wide range of surgical procedures. The staple-clip comprises a plurality of individual elements including a clip component and a securing or fixation member connected with the clip component to form a composite staple-clip. The composite staple-clip may be configured for use in both open and minimally invasive or laparoscopic surgeries. The staple-clip may be introduced to a surgical site in an un-assembled condition through a small port or trocar. An applier for the staple-clip comprising a pair of opposed jaw-like channels is provided to position and apply the clip component and the securing member The clip component is positioned around a target tissue and is compressed or clamped upon the tissue using only the force required for a specific surgical procedure such as occlusion, ligation or fixation. When the clip component is properly applied and the desired effects are observed, the securing member is urged forward and over the clip component to secure the staple-clip.

In one aspect of the invention, the clip component includes traction enhancement features including surface interruptions, bumps, valleys, ridges and the like. In another aspect of the invention, the clip component includes tissue-penetrating features similar to those of a staple. It is appreciated that with the staple-clip of the invention, the force required to constrict or occlude the tissue is separate from the force required to secure and maintain the staple-clip in position. That is, only the compressive force needed to perform a specific surgical procedure such as occlusion, ligation or fixation is applied to the body tissue, and the force normally required to secure and maintain a clip of the prior art is not applied since traction and security are supplied by the clip component and securing member of the staple-clip. As a result, the body tissue is not over-compressed and nourishment to the body tissue is maintained.

Other aspects of the invention include thumb actuated clip appliers for use in hand assisted laparoscopy (HAL). In one embodiment, a clip applier includes a handle and a thumb actuated mechanism that is used to slidably release clips onto a body tissue or vessel by sliding the thumb actuated mechanism forward and backward using only one hand. This design closes the jaws around the body tissue or vessel and allows a closed clip to slide into position. In another embodiment, a clip is provided having a first arm and a second arm folded over the first arm. The first arm includes a latch mechanism such as an inwardly turned portion or hook at its distal end that is configured to interlock or mate with a distal end of the second arm when the arms are clamped together. The latch mechanism operates in a similar way to a hair clip and responds to thumb pressure. An operator may single-handedly access the clip and slide it onto a body tissue or vessel as needed. The arms of the clip may include tissue-penetrating elements on the inner, opposed faces of the arms.

In another aspect of the invention, a two-stage clip is disclosed having a clip component and a staple component for securing the clip after it has been properly positioned. The clip component is formed from a first piece of material and includes opposed arms, each of which includes openings allowing penetration of legs of the staple component. The staple component is formed from a second piece of material and is used to puncture a body tissue or vessel and to interlock the clip component The arms of the clip component may include a latch mechanism at the distal ends to mate with each other when the arms are closed or clamped together. During use, the first stage closes the arms of the clip. After the first stage, the clip can still be safely removed. The second stage secures the clip permanently onto the body tissue or vessel by applying the staple component to the clip component. In another embodiment, a two-stage clip is formed entirely from a single piece of material and includes a first arm and an opposed second arm The second arm further includes securing elements, all of which are formed as an integral, one-piece construction. With this construction, the securing elements may still remain open after the first stage when the arms are clamped upon a body tissue or vessel. A second action then presses the securing elements into the body tissue or vessel.

These and other features and advantages of the invention will become more apparent with a discussion of preferred embodiments in reference to the associated drawings.

DESCRIPTION OF THE DRAWINGS

FIGS. 1(*a*) and 1(*b*) illustrate a typical surgical clip in an open condition and a closed condition, respectively;

FIG. 2 illustrates the movement and slippage of a typical surgical clip;

FIGS. 3(*a*) and 3(*b*) illustrate a typical surgical staple in an open condition and a closed condition, respectively;

FIGS. 4(*a*) and 4(*b*) illustrate a typical arrangement of open and closed surgical staples, respectively;

FIGS. 5(*a*) and 5(*b*) illustrate a typical surgical clip applier and staple applier, respectively;

FIG. 6(*a*) is a perspective view of the clip components and securing member of the staple-clip in accordance with an embodiment of the invention;

FIG. 6(*b*) is a perspective view of the assembled staple-clip of FIG. 6(*a*);

FIGS. 9(*b*), 9(*d*), 9(*f*) and 9(*h*) are end views of the staple-clip of FIGS. 9(*a*), 9(*c*), 9(*e*) and 9(*g*), respectively;

FIGS. 10(*c*) and 10(*d*) are side views of the clip of FIGS. 10(*a*) and 10(*b*), respectively, having pointed tissue-penetrating elements;

FIGS. 10(*e*) and 10(*f*) are end views of the clip of FIGS. 10(*c*) and 10(*d*), respectively;

FIGS. 11(*a*) and 11(*b*) are side views of the staple-clip before and after placement upon a body conduit or passage, respectively;

FIGS. 11(*c*) and 11(*d*) are end views of the staple-clip of FIGS. 11(*a*) and 11(*b*), respectively;

FIGS. 12(*a*) and 12(*b*) are schematic side views of a staple-clip applier in a closed and open condition, respectively;

FIGS. 12(*c*) and 12(*d*) are front, end views of the staple-clip applier of FIGS. 12(*a*) and 12(*b*), respectively;

DESCRIPTION OF PREFERRED EMBODIMENTS AND BEST MODE OF THE INVENTION

Figure 7:
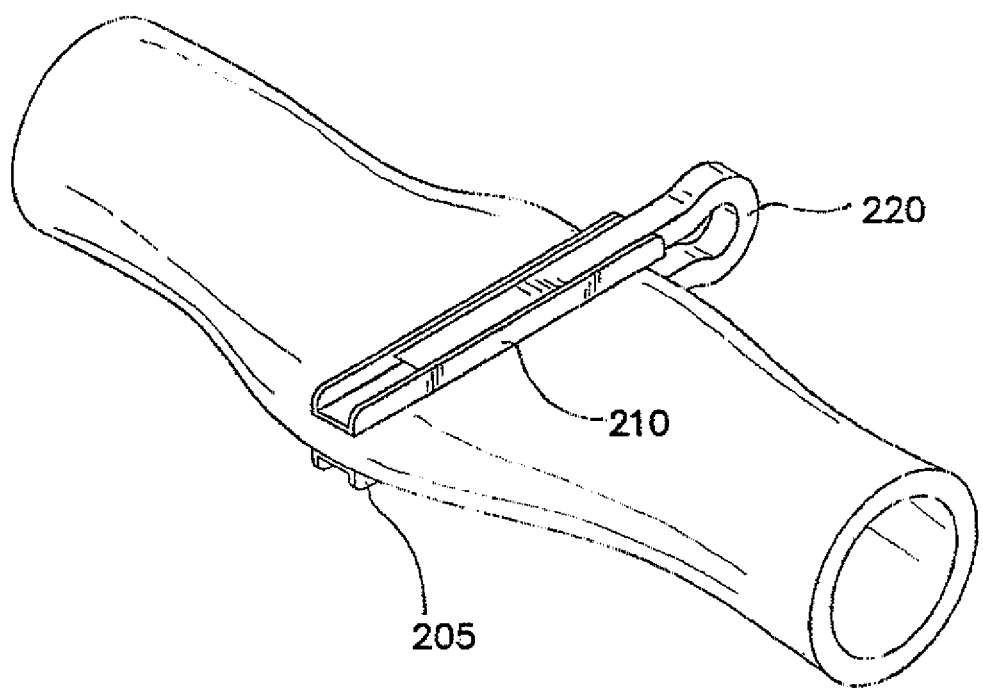
FIG. 7 is a perspective view of the assembled staple-clip of FIG. 6(*b*) placed upon a body conduit or passage.
Figure 8:
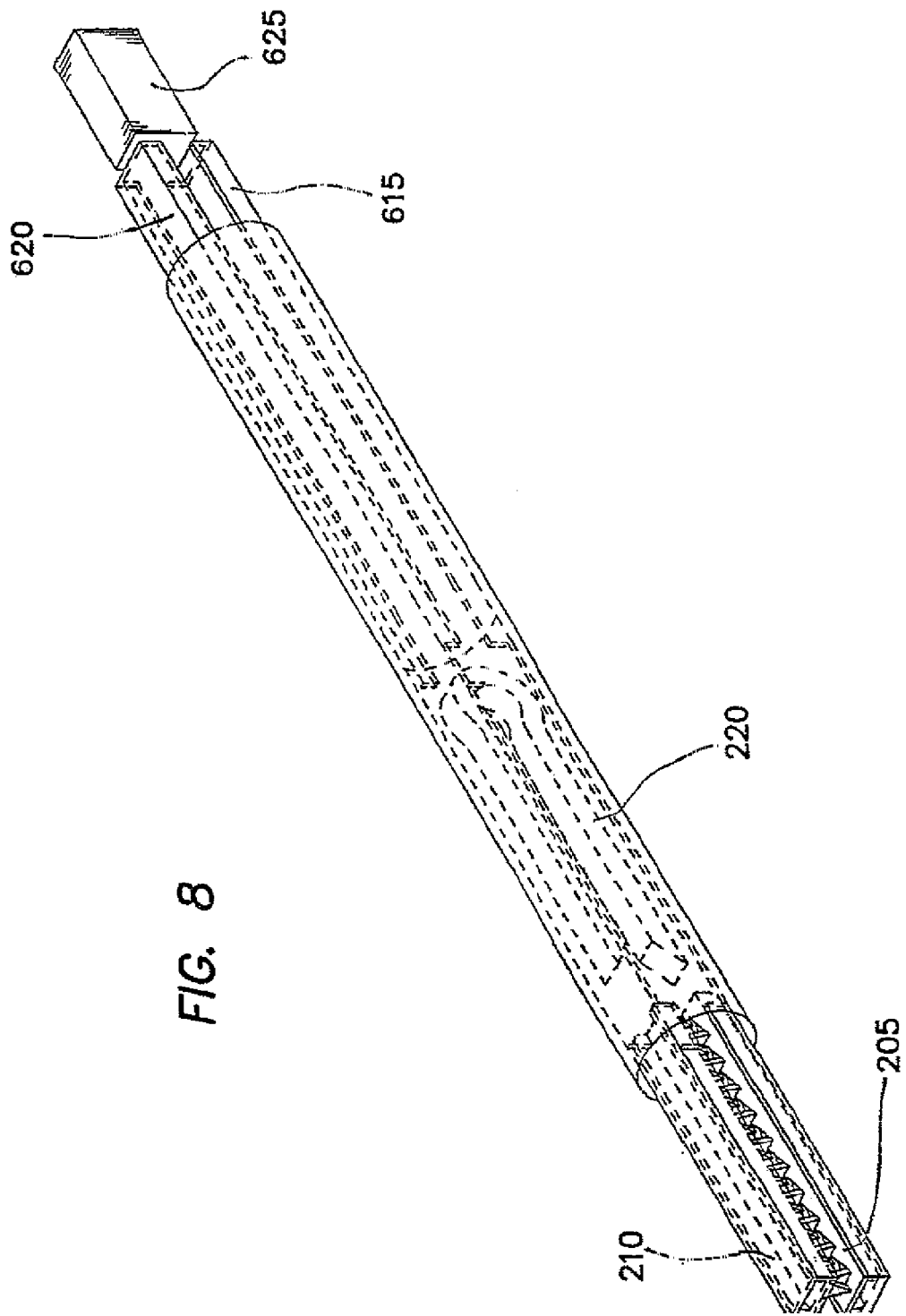
FIG. 8 is a perspective view of the staple-clip and applier configured for use in a minimally invasive surgical procedure.
Figure 9A:
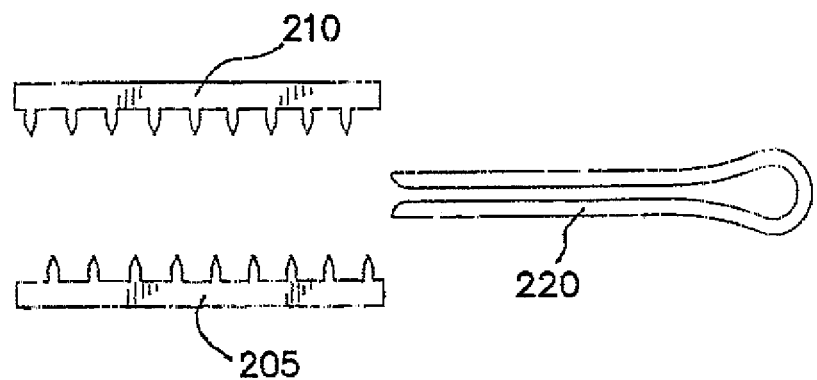
FIGS. 9(*a*), 9(*c*), 9(*e*) and 9(*g*) are side views of the staple-clip of the invention in an open, closing, closed and locked condition, respectively.
Figure 9B:
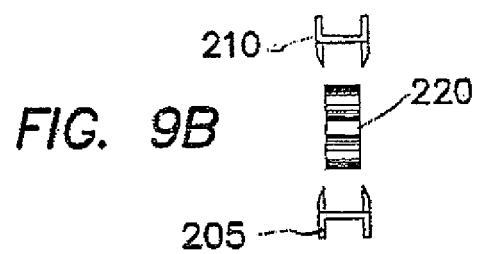
Figure 9C:
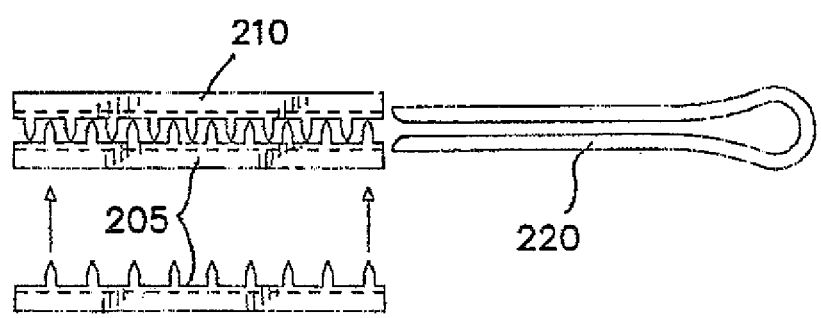
Figure 9D:
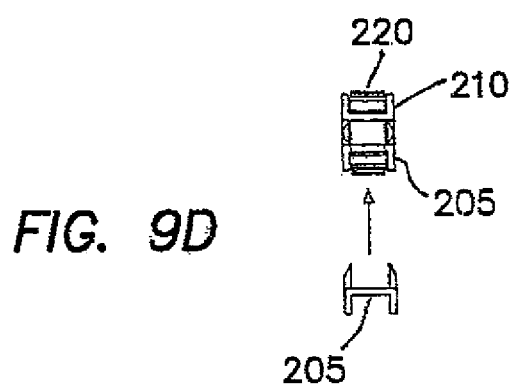
Figure 9E:
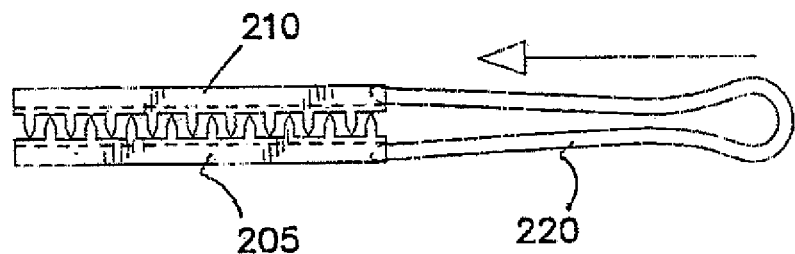
Figure 9F:
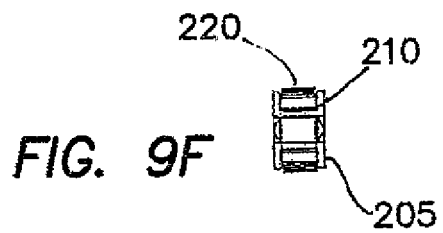
Figure 9G:
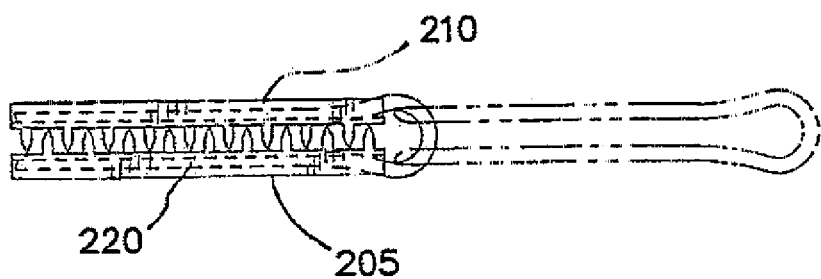
Figure 9H:
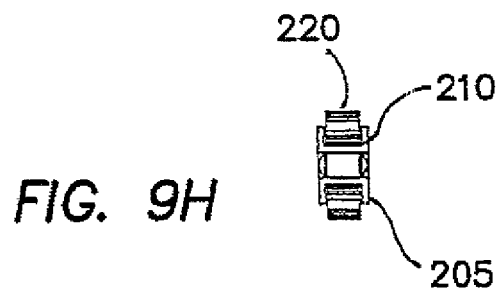
Figure 10A:
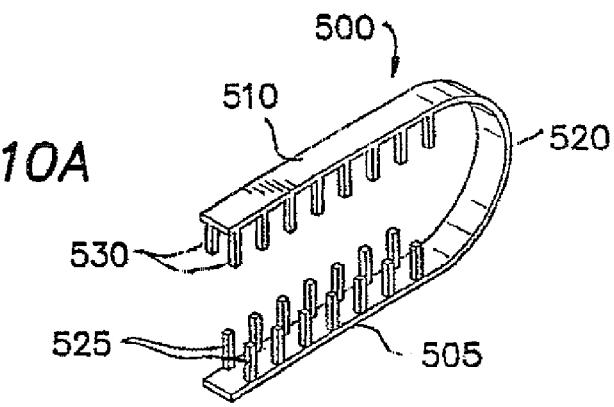
FIGS. 10(*a*) and 10(*b*) are perspective views of a clip in an open and closed condition, respectively, having a monolithic construction in accordance with another embodiment of the invention.
Figure 10C:
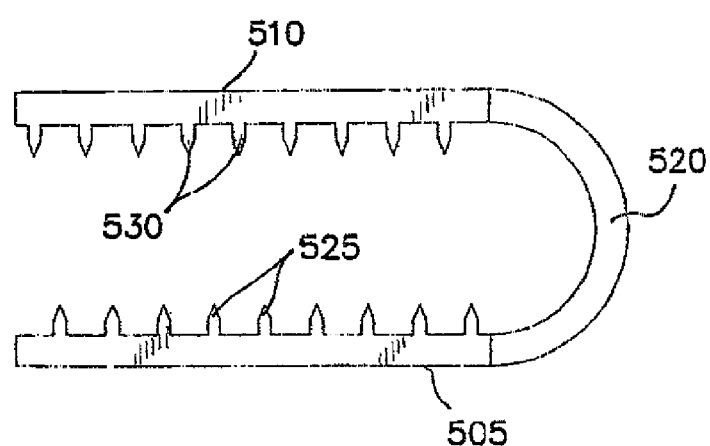
Figure 10E:
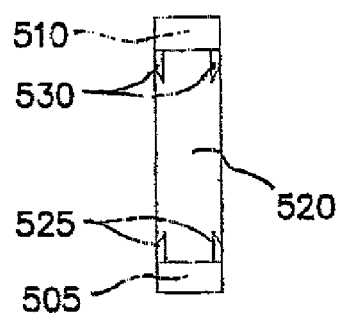
Figure 10B:
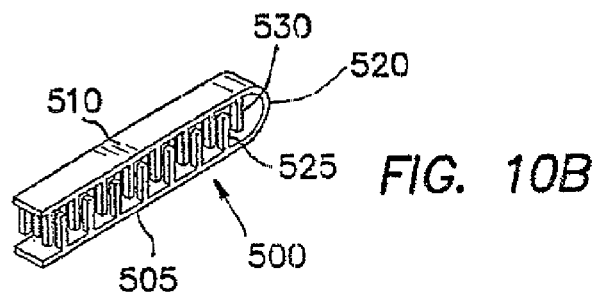
Figure 10D:
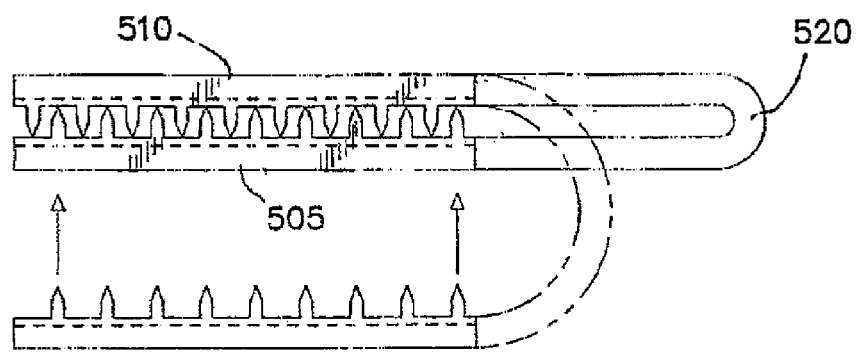
Figure 10F:
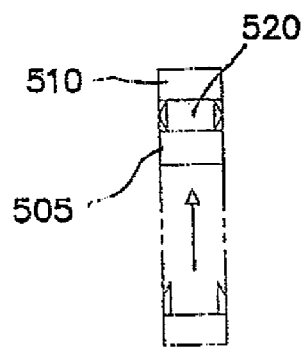

FIGS. 1 and 2 illustrate a surgical clip 10 of the prior art having a generally open shape including a first leg 15, a second leg 20 and a base 30 connecting the first leg 15 and the second leg 20. The clip 10 can be positioned around a body conduit or passage, e.g., a blood vessel, and compressed using a clip applier 150 as illustrated in FIG. 5(*a*). The clip applier 150 generally comprises an elongate shaft 155, sized and configured to fit through a surgical trocar port, a distal end 160 having a pair of opposed jaws 165, 167 and a proximal end 170 having a handle 180 to open and close the jaws 165, 167 The clip 10, held in an open condition, is supplied to the jaws 165, 167 either automatically or manually The clip 10 is advanced to a desired site and subsequently closed or compressed. With the first and second legs 15 and 20 properly formed, the jaws 165, 167 can be opened and moved away from the tissue leaving the clip 10 clamped around the tissue. The clip 10 derives its strength from the material from which it is made. The material chosen must be sufficiently malleable to allow the clip to be compressed as illustrated in FIG. 1(*b*) while preventing spring-back of the material after application of a compressive force.

There are many factors that must be considered in applying a surgical clip to a body tissue or vessel. First, the clip must be sufficiently wide to completely encompass the tissue. As illustrated in FIG. 1(*a*), the clip 10 must have an open area 50 that is wide enough to encompass the target tissue. Second, the clip must be compressible with a reasonable application force, i.e., a force that an operator feels comfortable applying to the body tissue. Third, the clip, once applied, must not move from the location where it was applied. As illustrated in FIG. 2, the clip 10 must not slip along axes 80(a) or 80(b) or slip off of body vessel 60. A fourth factor is that the clip 10 should not compress the body tissue so much that it constricts, interrupts or destroys the nourishment of the tissue. As can be seen, the above factors of clip-based ligation or fixation are difficult to achieve using a single wire-formed clip. Moreover, the issues of compression and traction must be separated if proper nourishment of the tissue is to be preserved while maintaining a secure placement of the clip.

Surgical staples are another device that is commonly used for occlusion, ligation and fixation of body tissues and vessels Referring to FIG. 3(a), a typical surgical staple 100 comprises generally straight, penetrating leg portions 110 and 120 connected together by a base portion 130. As the penetrating leg portions 110, 120 are applied to a body tissue or vessel, the leg portions advance through the tissue and are bent against the opposing jaw of the stapler and toward each other as illustrated in FIG. 3(b). The bending of the staple 100 forms a confinement of the body tissue that is, for the most part, independent of the compression of the tissue itself. FIG. 5(b) illustrates a laparoscopic stapler 190 that operates in much the same way as a clip applier. During use, the stapler 190 is advanced over a portion of body tissue and is compressed to deliver at least one, and more often several, penetrating surgical staples. See, for example, FIGS. 4(a) and 4(b). The compressed surgical staple 100 has a general shape of the capital letter "B" where fluid nourishment of the tissue is provided through open portions 140 of the folded staple 100. Surgical staples have proved to be effective and are a standard in surgery. However, the staplers used for applying the staples are often bulky and require a very strong closing or compressing force, which is not ideal for minimally invasive or laparoscopic surgeries. Accordingly, there is a need in the art for a device having features and advantages of both the staple and clip. The staple/clip would provide good traction to prevent the device from moving or dislodging from the body tissue while maintaining proper nourishment to the tissue. In addition, the force required to constrict or occlude the body tissue would be separated from the force required to secure and maintain the device in position. Specifically, the portion of tissue to be treated would not be compressed more than is necessary to achieve the desired result.

FIG. 6(a) illustrates a surgical staple-clip 200 in accordance with a first embodiment of the invention. The staple-clip 200 comprises a first tissue-engaging member 205, a second tissue-engaging member 210 opposed to the first tissue-engaging member 205, and a securing or fixation member 220 for securing the first and second tissue-engaging members 205, 210. The first tissue-engaging member 205 comprises generally opposed walls 230, 232 and a connecting wall 234 that together define an elongate channel 236. The second tissue-engaging member 210 is similar to the first tissue-engaging member 205 and comprises generally opposed walls 240, 242 and a connecting wall 244 that together define an elongate channel 246. The tissue-engaging members 205, 210 are normally held such that the front faces of the connecting walls 234, 244, respectively, are opposed to each other. The opposing front faces of the connecting walls 234, 244 may include a plurality of tissue-penetrating elements 238, 248, respectively.

An advantage of the staple-clip of the invention is it provides good traction without requiring an excessive compressive force to be applied to the staple-clip In particular, the securing member 220 is sized and configured to slide into the elongate channels 236, 246 to securely clamp the tissue-engaging members 205, 210 around a body tissue or vessel with minimal compressive force. More specifically, the force required to secure and maintain the staple-clip (to provide adequate traction) is independent from the force required to constrict or occlude a body tissue or vessel. With the staple-clip of the invention, only the compressive force needed to perform a specific surgical procedure such as occlusion, ligation or fixation is applied to the body tissue, and the force normally required to secure and maintain a clip of the prior art is not applied since traction and security are supplied by the tissue-engaging members 205, 210. In other words, the staple-clip of the present invention provides the necessary traction without requiring an excessive compressive force to keep the staple-clip from moving or becoming loose. As a result, nourishment of the lightly compressed tissue is maintained and tissue necrosis due to over-compression is eliminated.

Figure 13B:
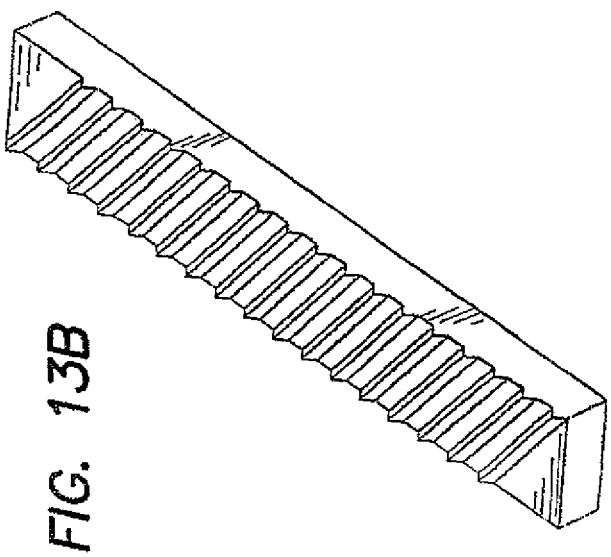
FIGS. 13(*a*) and 13(*b*) are perspective views of the tissue contacting face portions of a staple-clip in another aspect of the invention.
Figure 13A:
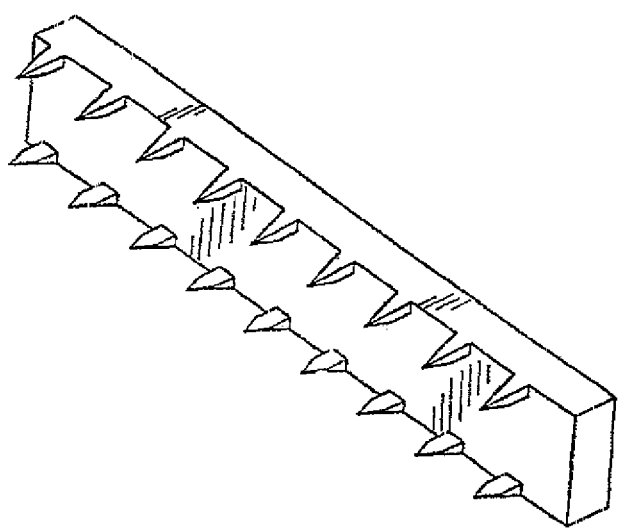
Figure 14:
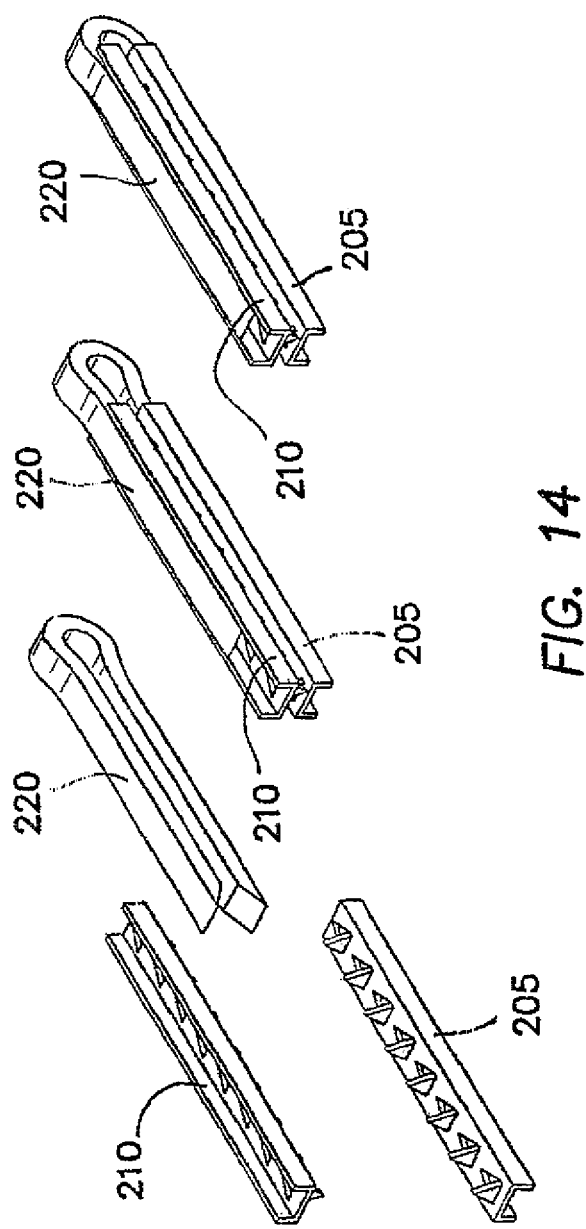
FIG. 14 illustrates the sequence of placing the securing member upon the tissue-engaging members of the staple-clip of the invention.
Figure 15A:
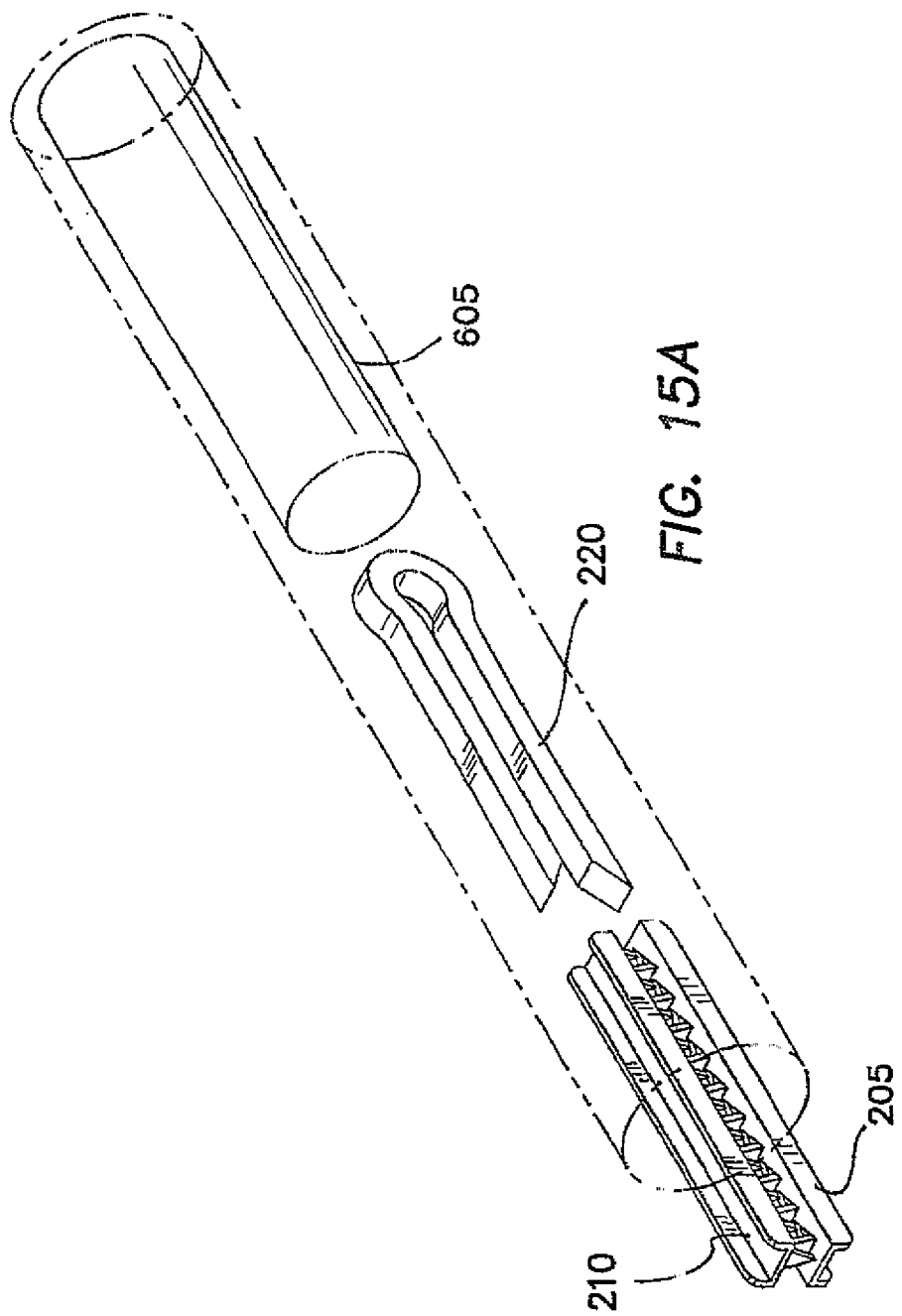
FIGS. 15(*a*), 15(*b*) and 15(*c*) illustrate the invention sized and configured to pass through a small trocar port in a first condition, second condition and final condition, respectively.
Figure 15B:
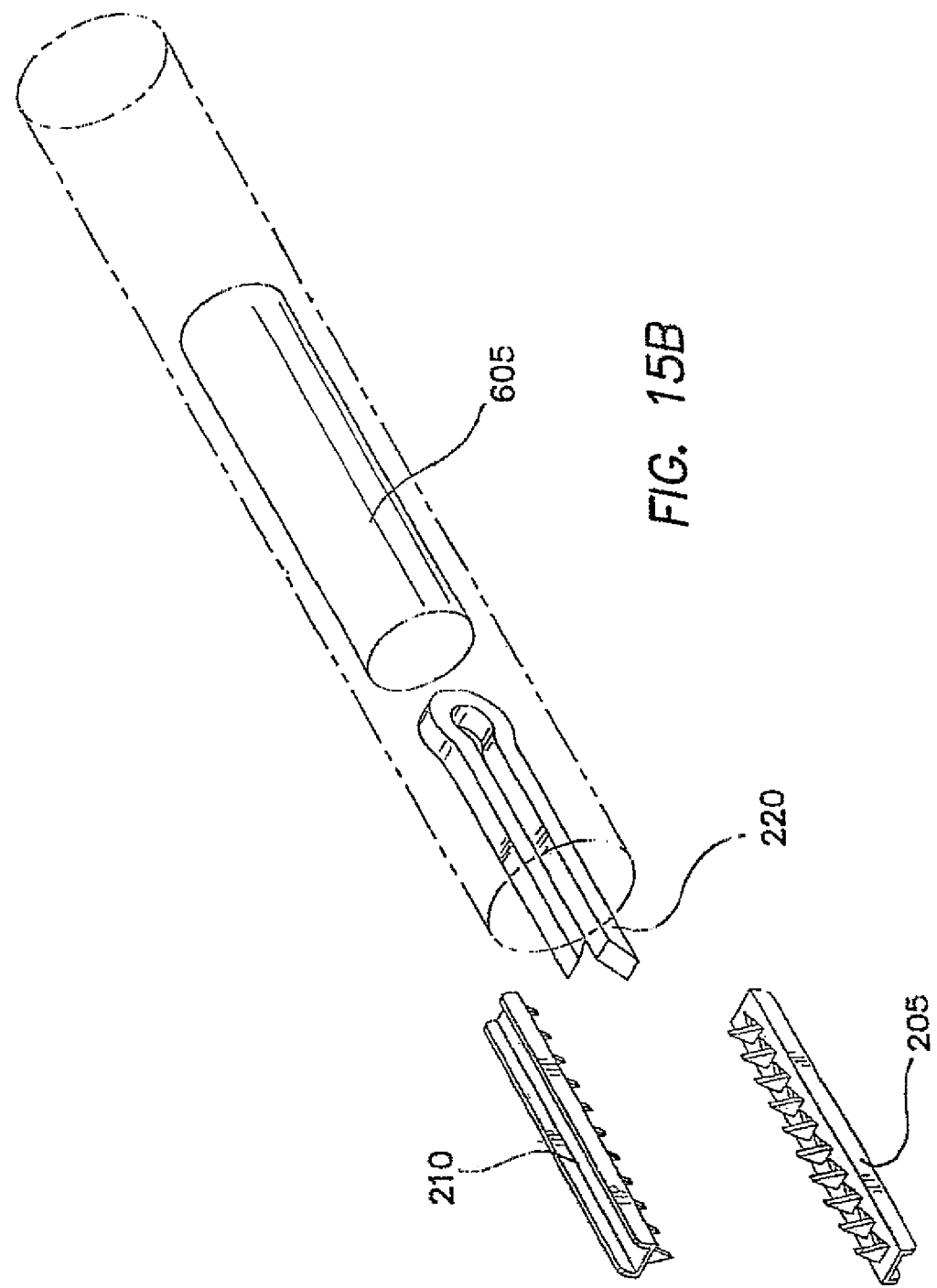
Figure 16:
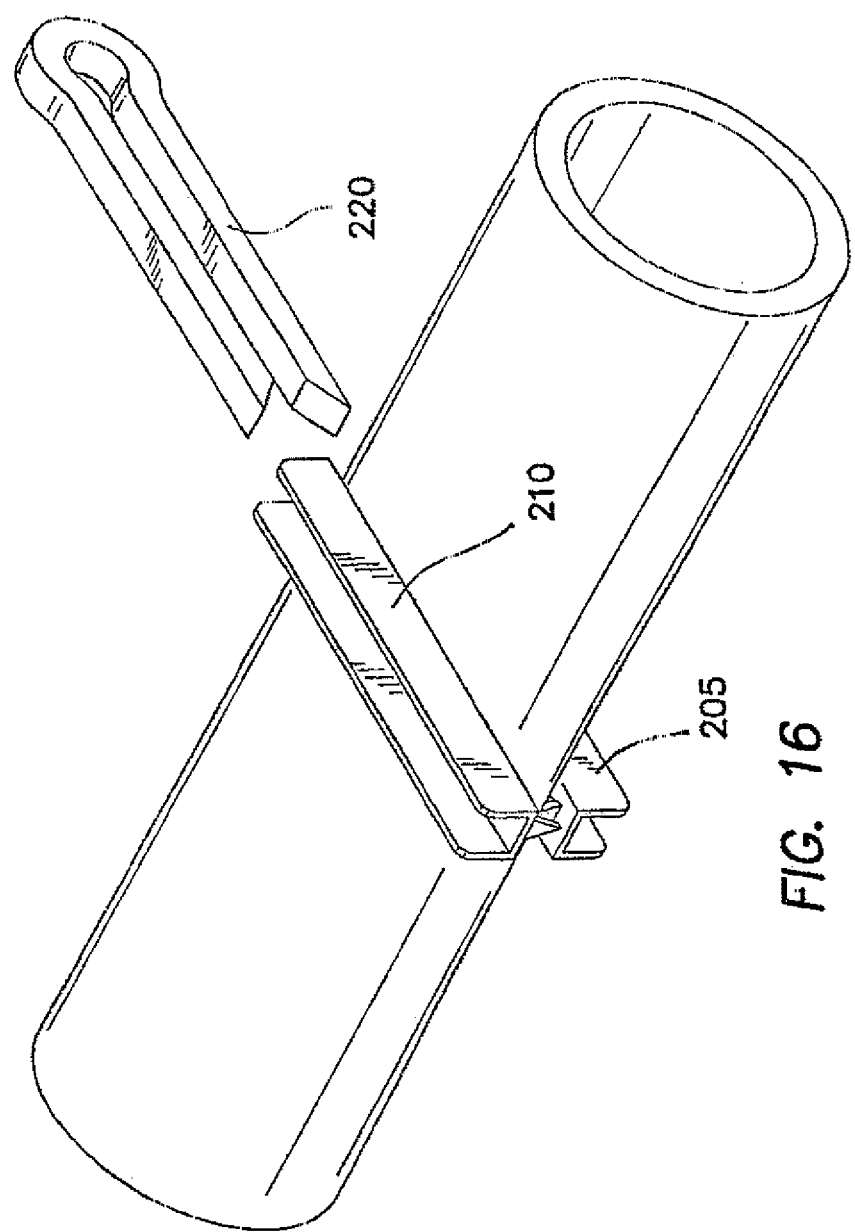
FIG. 16 illustrates placement of a single staple-clip of the invention.

In another aspect of the invention, the tissue-engaging members include traction enhancing features including bumps, ridges, slots, holes, etc. as generally illustrated in FIGS. 13(a) and 13(b). The traction enhancing features are sized and configured to grip tissue and provide traction and security beyond that which might be achieved by over-compressing a typical clip. The securing member 220 may be a spring-clip or a deformable clip acting as a retention member and providing a uniform pressure across the occluded tissue or vessel to prevent loosening of the staple-clip 200 over time as illustrated in FIGS. 7, 9(a)-9(h) and 14. The tissue-penetrating elements 238, 248 are configured to penetrate the tissue and to prevent the tissue from moving or sliding when clamped as illustrated in FIGS. 11(a)-11(d), 16 and 17.

It is appreciated that the connecting walls 234, 244 and the respective tissue-penetrating elements 238, 248 may be formed as an integral, one-piece construction. It is further appreciated that the number of rows of tissue-penetrating elements and the number of tissue-penetrating elements per row may vary according to each application and the shape and size of the clip and body tissue It is further noted that the tissue-penetrating elements in each row may be aligned or staggered as desired. The tissue-engaging members 205, 210 and the securing member 220 may have cross-sections of any configuration including polygonal, circular and elliptical configurations.

Referring to FIG. 10, there is shown a monolithic staple-clip 500 in accordance with another aspect of the invention. The monolithic staple-clip 500 has a general shape of the capital letter "U". The staple-clip 500 comprises a first tissue-engaging portion or leg 505, an opposed second tissue-engaging portion or leg 510 and a deformable connecting portion 520 connecting the first and second tissue-engaging portions 505 and 510 Each of the opposing faces of the tissue-engaging portions 505, 510 comprises a plurality of tissue penetrating elements or protrusions 525, 530, respectively. The protrusions are sized and configured to penetrate tissue that is captured between the tissue-engaging portions and provide traction and security beyond that which might be achieved by over-compressing a typical clip. Similar to other aspects of the invention, only the force required to perform a specific surgical procedure such as occlusion, ligation or fixation is applied to a body tissue and the force previously needed to secure and maintain the clip is no longer applied. Nourishment of the lightly compressed tissue is thus maintained and tissue necrosis due to over-compression is eliminated.

The monolithic staple-clip 500 may be formed from a flat metal sheet that is die-cut, stamped or etched forming a first notched or toothed portion, a smooth connecting portion and a second notched or toothed portion. The notches or teeth of the first and second portions are then bent so as to extend in the same direction or plane and to form channels within the notches or teeth. The staple-clip is then formed in a U-shape by bending the connecting portion so that the notches or teeth of the two tissue-engaging portions are opposed. A preferred embodiment of the monolithic staple-clip comprises a malleable material such as Titanium or stainless steel. Other materials include any medically acceptable metal or plastic material that is ductile, malleable or deformable.

It is appreciated that the staple-clips of the invention can be applied to a body tissue or vessel using an applier 600 as illustrated in FIGS. 12(a)-12(d) The staple-clip applier 600 generally comprises an elongate shaft 605, sized and configured to fit through a surgical trocar port, a distal end 610 having a pair of opposed jaws 615, 620, and a proximal end (not shown) having a handle to open and close the jaws 615, 620. The staple-clip applier 600 further comprises a sliding member 625 to advance the securing member 220 over the tissue-engaging members 205, 210 after closure of the jaws 615, 620 as further described below. The jaws 615, 620 operate to apply the tissue-engaging members 205, 210, respectively, around a target body tissue or vessel The tissue-engaging members are supplied to the jaws either manually or automatically. With the tissue-engaging members 205, 210 properly placed, the jaws 615, 620 can be compressed using only the force required for a specific surgical procedure such as occlusion, ligation or fixation. When the tissue-engaging members 205, 210 are properly applied, the sliding member 625 can then urge the securing member 220 forward and over the tissue-engaging members 205, 210 to secure the staple-clip 200 as illustrated in FIGS. 9(a)-9(h), 11(a)-11(d) and 14. The tissue-engaging members 205, 210 and securing member 220 may be introduced to a surgical site in an un-assembled condition through a small port or trocar FIGS. 8 and 15(a)-15(c) further illustrate the staple-clip and applier sized and configured for use in a minimally invasive or laparoscopic surgical procedure.

Figure 17:
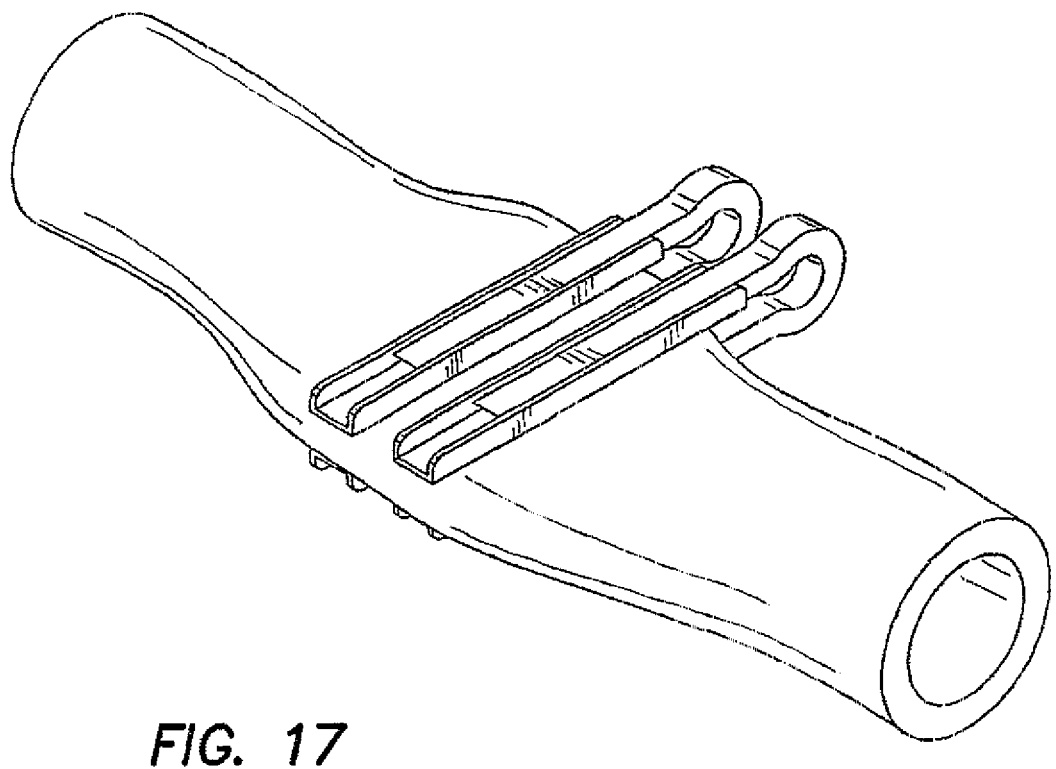
FIG. 17 illustrates parallel placement of the staple-clips of the invention.
Figure 18:
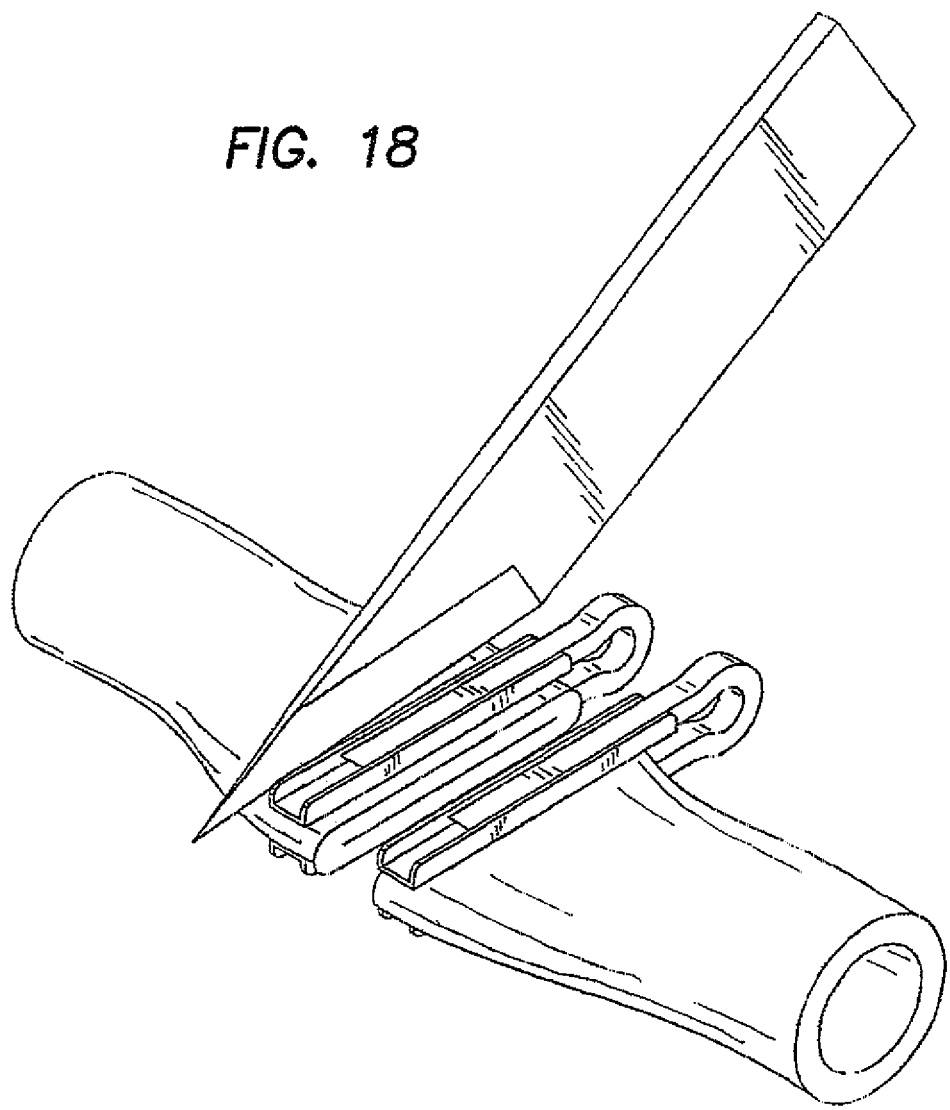
FIG. 18 illustrates parallel placement of the staple-clips of the invention with a cutting element placed between the staple-clips.

Multiple staple-clips may also be loaded in a staple-clip applier and advanced individually or simultaneously between the jaws. In the case of simultaneously applying the staple-clips, the applier must include a plurality of slots in the opposed jaws to receive the multiple staple-clips. A cutting member such as a blade may be included in the applier to be advanced between the staple-clips after they have been applied to transect the body tissue between the staple-clips as illustrated in FIGS. 17 and 18.

Figure 19:
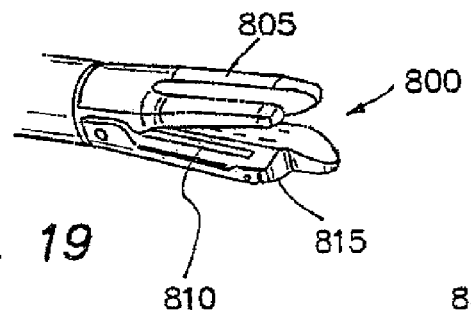
FIG. 19 illustrates a laparoscopic stapler configured for use in donor nephrectomy in accordance with another aspect of the invention.

In another aspect of the invention, FIG. 19 depicts a traditional laparoscopic stapler 800 that is configured specifically for donor nephrectomy. The stapler 800 includes a plurality of rows of staples on the patient side 805 and a temporary clip 810 that substitutes for a typical set of staples on the kidney side 815. The stapler 800 operates like existing place and cut staplers with the exception that a temporary clip or clips 810 replace the set of staples on the kidney side 815. The temporary clip 810 may be a staple cartridge configured for use in donor nephrectomy. An advantage of this configuration is it salvages a greater portion of the vessel for the transplant procedure.

Figure 20B:
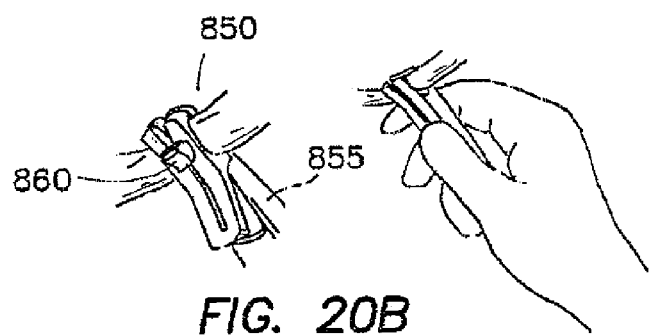
FIGS. 20(*a*)-20(*e*) illustrate various thumb actuated clip appliers for use in hand assisted laparoscopy (HAL) in accordance with additional aspects of the invention.
Figure 20A:
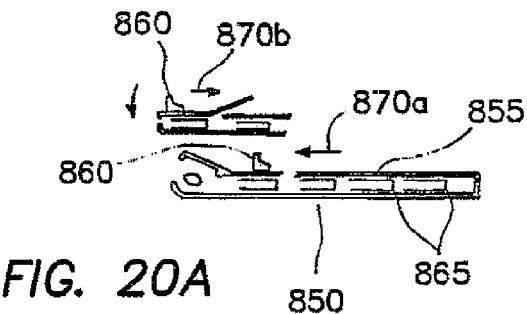
Figure 20D:
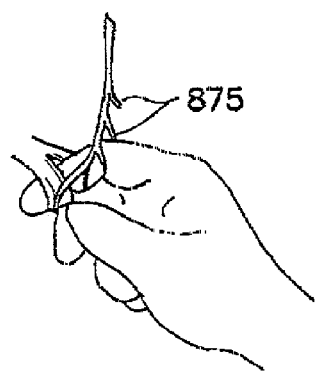
Figure 20C:
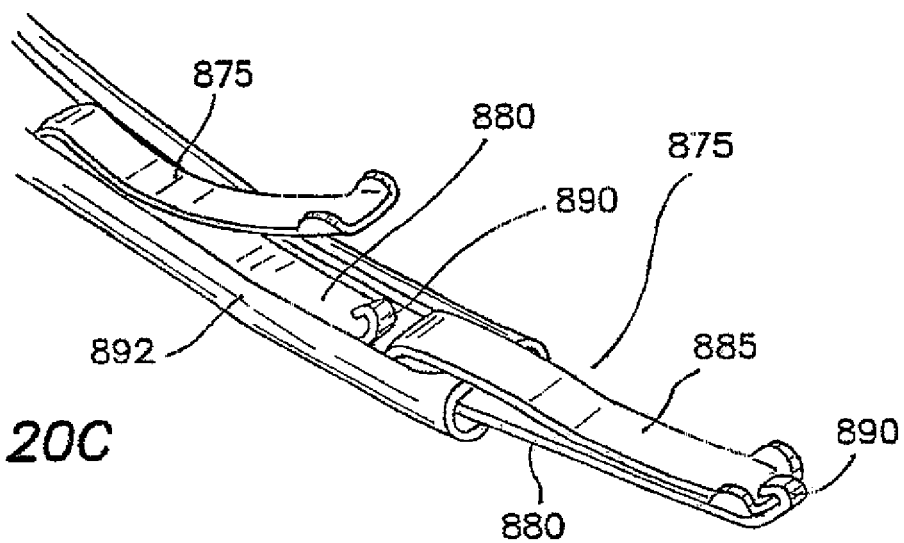

Another aspect of the invention is directed to hand assisted laparoscopy (HAL), the widespread acceptance of which has created many opportunities for surgical advancement utilizing single hand procedures. FIGS. 20(a)-20(e) illustrate thumb actuated clip appliers 850, 875 and 895 in accordance with the teachings of the invention. The clip applier 850 includes a handle 855 and a thumb actuated mechanism 860. An operator can slidably release clips 865 onto a vessel by sliding the thumb actuated mechanism 860 forward 870a and backward 870b using only one hand as illustrated in FIGS. 20(a)-20(b). This design closes the jaws around the vessel and allows a closed clip to slide into position. The handle 855 also serves as a reservoir for additional clips 865. The clip 875 is also designed for HAL applications and includes a first arm 880 and a second arm 885 folded over the first arm 880. The first arm 880 includes a latch mechanism 890 such as an inwardly turned portion or hook at its distal end that is configured to interlock or mate with a distal end of the second arm 885 when the arms are clamped together. The latch mechanism 890 operates in a similar way to a hair clip and responds to thumb pressure. An operator may single-handedly access the clip 875 and slide it onto a body tissue or vessel as needed.

Figure 20E:
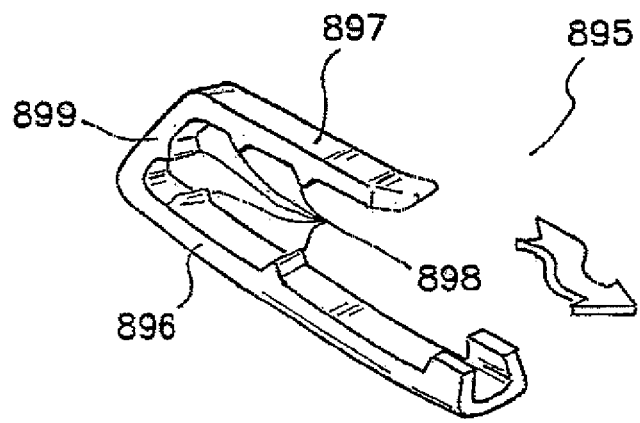

A plurality of clips 875 may be strung end-to-end in a clip sleeve 892 suspended through an open port. An advantage of the clip 875 is there is no instrument to misplace. The clip sleeve 892 holding the clips 875 can also be withdrawn or fed through any open port or trocar The clip sleeve 892 can also be designed to keep the clips 875 partially closed, enabling the use of smaller ports or trocars. The clip 895 as illustrated in FIG. 20(e) is similar to the clip 875 but further includes tissue-penetrating elements 898 on the inner faces of arms 896, 897. The clip 895 may also include a third arm 899 connecting the arms 896, 897.

Figure 21:
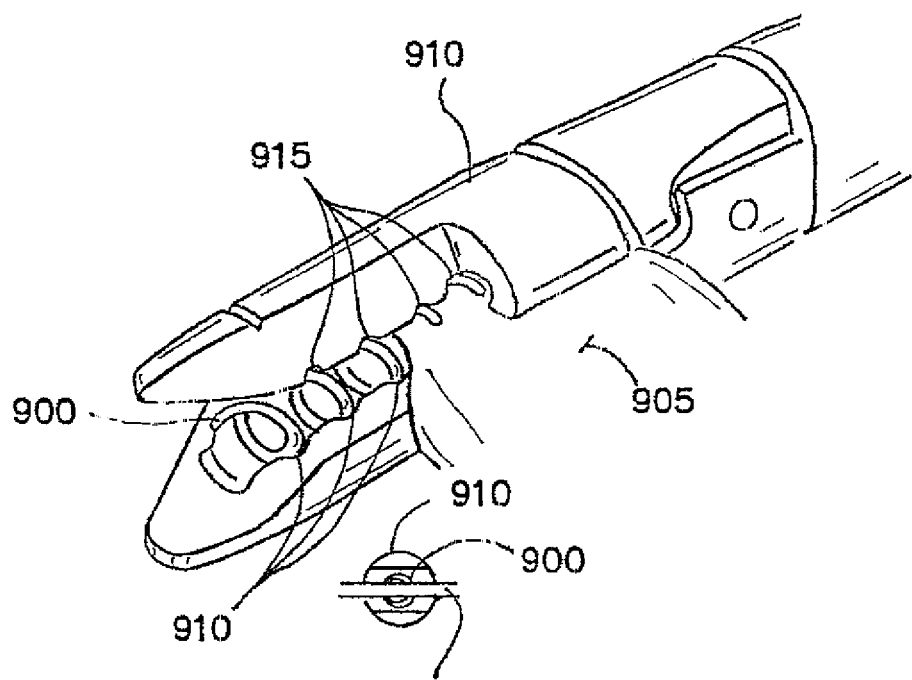
FIG. 21 illustrates a spring like coil for suturing a body tissue or vessel in accordance with another aspect of the invention.

In another aspect of the invention as illustrated in FIG. 21, a spring like coil 900 is used for suturing a body tissue or vessel in place of clips and staples. The spring like coil 900 is applied onto a body tissue or vessel 905 by using a stapler 910 having grooved jaws 910, 915. The spring like coil 900 is preferably loaded or twisted into one of the grooved jaws 910, 915, which is then compressed or clamped against the other grooved jaw to constrict or occlude the vessel 905 An advantage of this design is closure of the coil 900 provides a stitch like nature that replicates a uniformly applied suture. In one configuration, a single coil is inserted in place of each suture. It is appreciated that a single coil or multiple coils may be loaded into the grooved jaws of a stapler for each specific surgical procedure or closure.

Figure 22:
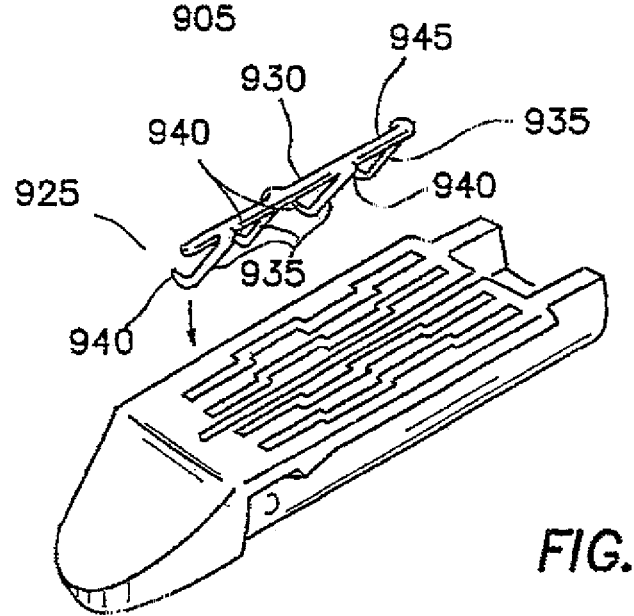
FIG. 22 illustrates a plurality of staples formed from a single piece of material in accordance with another aspect of the invention.

In yet another aspect of the invention, FIG. 22 illustrates multiple staples 925 formed from a single piece of material 930 to reduce the high manufacturing costs associated with current stapler cartridges. These costs savings translate to increased margins or reduced product cost. Each of the staples 925 has an angled leg 935 and an inclined rail 940 for easy push up and closure by a stapler. The staples 925 all share a common portion 945, which allows the row of staples to be formed as an integral, one-piece construction The staples 925 can also be formed to offset each other and to emulate multiple rows. An advantage of this aspect of the invention is it provides a compact cartridge that is suitable for donor nephrectomy.

Figure 23:
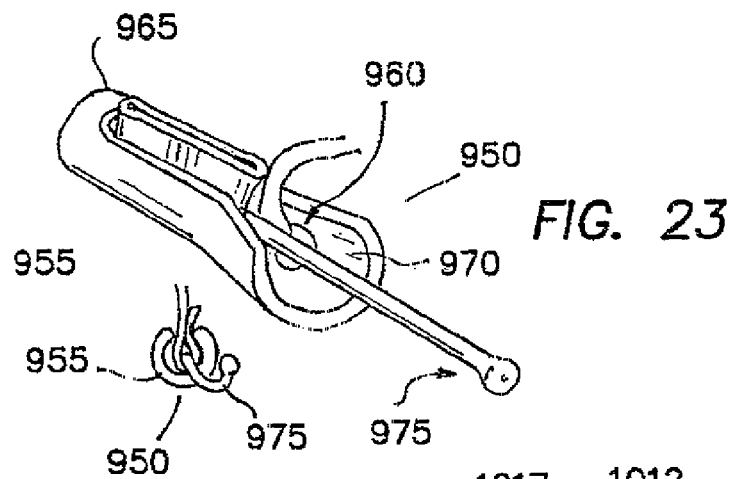
FIG. 23 illustrates a temporary HAL clamp for use in donor nephrectomy in accordance with another aspect of the invention.

FIG. 23 illustrates a temporary HAL clamp 950 for use in donor nephrectomy in accordance with another aspect of the invention. The clamp 950 includes a tubular section 955 defining an opening 960 extending from a proximal end 965 to a distal end 970, and a lead-in wire 975 operably attached to the proximal end 965 The lead-in wire 975 is movable between an open position and a closed position. When closed, the lead-in wire 975 is slidably received and secured in the opening 960 of the tubular section 955. During use, an operator may manually wrap a vessel or vessels (e.g., the renal artery and vein can be cinched together into the clamp) around the lead-in wire 975 and secure the wire 975 in the opening 960 of the tubular section 955. The lead-in wire 975 may be bent against the wall of the tubular section 955 to further secure the vessel(s) for kidney removal and transport.

Figure 24:
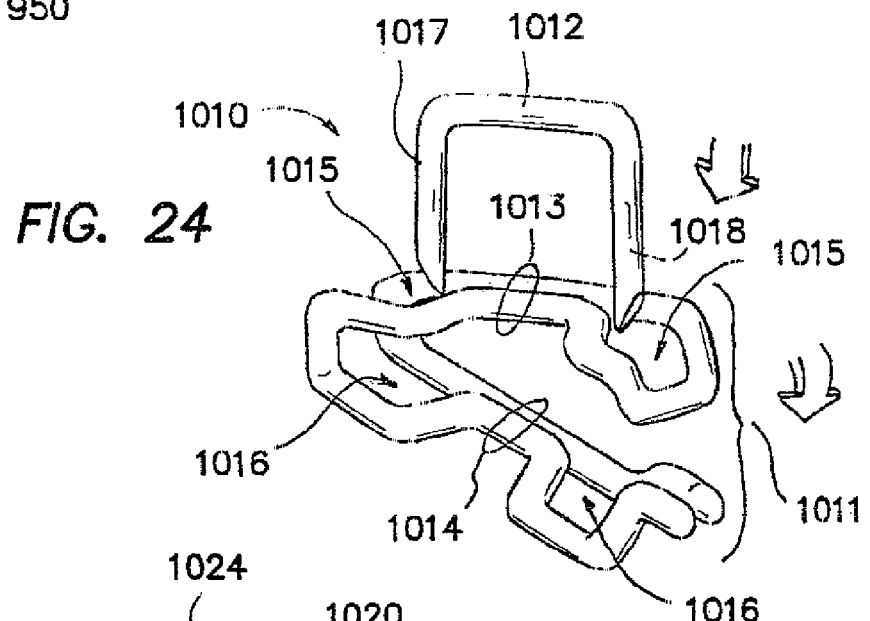
FIGS. 24-26 illustrate various two-stage staple-clips in accordance with additional aspects of the invention.
Figure 25:
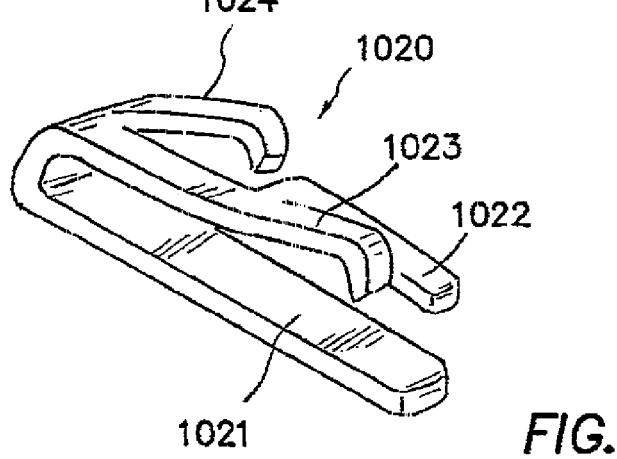
Figure 26:
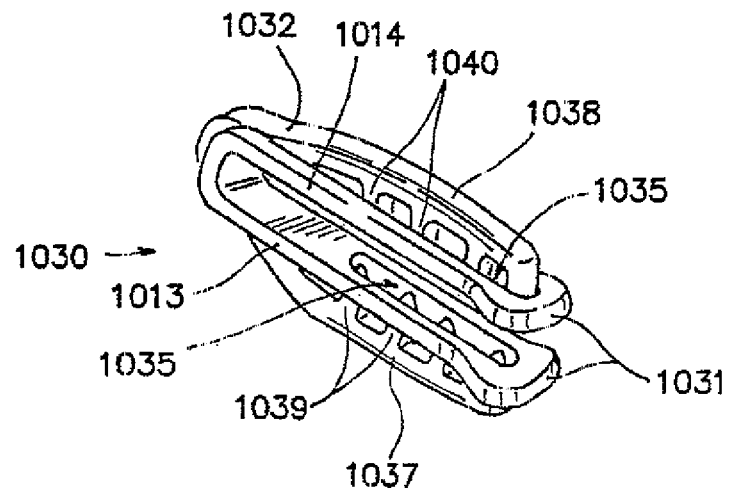

FIGS. 24, 25 and 26 illustrate two-stage clips 1010, 1020 and 1030, respectively, in accordance with additional embodiments of the invention. The clips 1010, 1020 and 1030 require an applier (not shown) for placement onto a body tissue or vessel. The clip 1010 includes a clip component 1011 and a staple 1012 for securing the clip after it has been properly positioned. The clip component 1011 is formed from a single wire and includes opposed arms 1013, 1014. Each of the arms 1013, 1014 includes openings 1015, 1016, respectively, allowing penetration of legs 1017, 1018 of the staple 1012. The staple 1012 is formed from a second wire and is used to puncture the body tissue or vessel and interlock the clip component 1011. The arms 1013, 1014 may include a latch mechanism at the distal ends to mate with each other when the arms are closed or clamped together. During use, the first stage closes the arms 1013, 1014 of the clip. After the first stage, the clip can still be safely removed The second stage secures the clip permanently onto the body tissue or vessel by applying the staple 1012 to the clip component 1011.

The two-stage clip 1020 as shown in FIG. 25 is formed entirely from a single piece of material and includes a first arm 1021 and an opposed second arm 1022. The second arm 1022 further includes securing elements 1023, 1024, all of which are formed as an integral, one-piece construction. With this construction, the securing elements 1023, 1024 may still remain at an angle after the first stage (when the arms 1021 and 1022 are clamped upon a body tissue or vessel). A second action then presses the securing elements 1023, 1024 into the body tissue or vessel. The clip 1030 as shown in FIG. 26 is similar to the clip 1010 and includes a clip component 1031 and a staple component 1032 for securing the clip after it has been properly positioned. The clip component 1031 includes opposed arms 1013, 1014 defining openings 1035, 1036, respectively. The staple component 1032 includes opposed arms 1037, 1038 having tissue-securing elements 1039, 1040, respectively, which operate to secure the clip onto a body tissue or vessel through the openings 1035, 1036. The clip 1030 may be formed in sheet stock.

Figure 27:
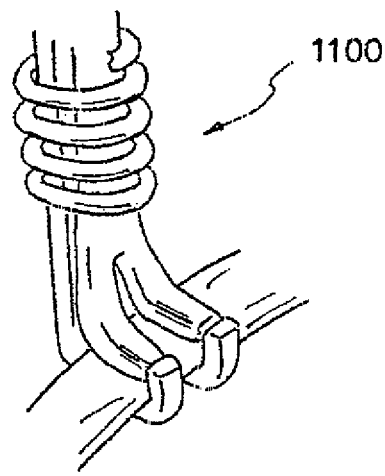
FIG. 27 illustrates a holder to press a body tissue flat and to provide clearance during placement of a staple-clip having sharp features.

FIG. 27 illustrates a tissue holder 1100 for use with staple-clips that may include sharp features, e.g., tissue-penetrating elements, that can potentially injure tissue during a surgical procedure. In particular, the tissue holder 1100 is used to press a body tissue flat and to provide clearance during placement of a staple-clip.

Although exemplary embodiments of the invention have been shown and described, many alterations and modifications may be made by those having ordinary skill in the art without departing from the spirit and scope of the invention. Therefore, it must be understood that the illustrated embodiments have been set forth only for the purposes of examples and that they should not be taken as limiting the invention. In addition, the words used in this specification to describe the invention and its various embodiments are to be understood not only in the sense of their commonly defined meanings, but to include any special definition given in this specification.

The invention claimed is:

1. A medical device to constrict or occlude a body tissue or vessel, comprising:
  a first tissue-engaging member having a first end, a second end opposite the first end, opposed walls and a first connecting wall defining a first elongate channel extending from the first end to the second end and the first elongate channel being open at the first end and the second end;
  a second tissue-engaging member opposed to the first tissue-engaging member having a first end, a second end opposite the first end, opposed walls and a second connecting wall defining a second elongate channel extending from the first end to the second end and the second elongate channel being open at the first end and the second end; and
  a securing member for securing the first and the second tissue-engaging members such that front faces of the first and the second connecting walls are opposed to each other, the securing member comprising a spring clip generating a securing force;
  wherein the securing member has a distal-most face defining a tapered surface that is slidably advanceable into the first and the second elongate channels to securely clamp the first and the second tissue-engaging members around the body tissue or vessel.

2. The medical device of claim 1, wherein each of the front faces of the first and the second connecting walls includes a plurality of tissue-penetrating elements.

3. The medical device of claim 2, wherein the first and the second connecting walls and the tissue-penetrating elements are formed as an integral, one-piece construction.

4. The medical device of claim 2, wherein the tissue-penetrating elements are formed in a plurality of rows.

5. The medical device of claim 4, wherein the number of tissue-penetrating elements per row and the number of rows vary according to each application.

6. The medical device of claim 4, wherein the tissue-penetrating elements are aligned or staggered.

7. The medical device of claim 2, wherein the tissue-penetrating elements and the securing member have cross-sections of any configuration including polygonal, circular and elliptical configurations.

8. The medical device of claim 1, wherein the force required to secure and maintain adequate traction is independent from a force required to constrict or occlude the body tissue or vessel.

9. The medical device of claim 8, wherein only a compressive force needed to perform a specific surgical procedure such as occlusion, ligation or fixation is applied to the body tissue.

10. The medical device of claim 9, wherein tissue necrosis due to over-compression is eliminated.

11. The medical device of claim 1, wherein at least one of the first and the second tissue engaging-members includes a plurality of at least one of bumps, ridges, slots, and holes.

12. The medical device of claim 1, wherein the securing member provides uniform pressure across the occluded tissue or vessel.

13. The medical device of claim 1, wherein the first elongate channel defines a first longitudinal axis, the second elongate channel defines a second longitudinal axis, and the securing member is an elongate member sized and configured to slide into the first elongate channel and the second elongate channel and to extend along the first longitudinal axis and the second longitudinal axis to secure the first tissue-engaging member and the second tissue-engaging member.

14. The medical device of claim 1, wherein the first tissue-engaging member, the second tissue-engaging member, and the securing member are sized and configured to be introduced to the body tissue or vessel through a surgical port in an unassembled configuration.

15. A medical device to constrict or occlude a body tissue or vessel, comprising:
  a first tissue-engaging portion having a first end and a second end opposite the first end and a first face extending from the first end to the second end, the first face including a plurality of tissue penetrating elements or protrusions;

a second tissue-engaging portion opposing the first tissue-engaging portion having a first end and a second end opposite the first end and a second face extending from the first end to the second end, the second face including a plurality of tissue penetrating elements or protrusions; and a spring clip comprising a distal-most face defining a tapered surface slidably advanceable over the first and the second tissue-engaging portions, the spring clip providing a substantially uniform securing pressure along the first tissue-engaging portion from the first end to the second end of the first tissue-engaging portion and along the second tissue-engaging portion from the first end to the second end of the second tissue-engaging portion.

16. The medical device of claim 15, wherein only a force required to perform a specific surgical procedure such as occlusion, ligation or fixation is applied to the body tissue or vessel.

17. The medical device of claim 16, wherein tissue necrosis due to over-compression is eliminated.

18. The medical device of claim 15, wherein the device is formed from any medically acceptable metal or plastic material.

19. The medical device of claim 18, wherein the metal includes titanium and stainless steel.

20. The medical device of claim 15, wherein the spring clip is slidably couplable with the first and the second tissue-engaging portions between an un-assembled condition and an assembled condition in which the spring clip is advanced over the first and the second tissue-engaging portions such that surfaces of the spring clip engagingly contact the first and second tissue-engaging portions from the first end to the second end of the first tissue-engaging portion and from the first end to the second end of the second tissue-engaging portion to provide the substantially uniform pressure.

21. The medical device of claim 15, wherein the first face of the first tissue-engaging portion is integrally formed with the plurality of tissue penetrating elements of the first face in a one-piece construction.

\* \* \* \* \*

UNITED STATES PATENT AND TRADEMARK OFFICE
CERTIFICATE OF CORRECTION

PATENT NO. : 8,998,935 B2
APPLICATION NO. : 12/200582
DATED : April 7, 2015
INVENTOR(S) : Charles C. Hart Page 1 of 1

It is certified that error appears in the above-identified patent and that said Letters Patent is hereby corrected as shown below:

Specification:

Column 1, line 28: Please add a --.-- after "the clips"

Column 1, line 42: Please add a --.-- after "surgical procedure"

Column 2, line 18: Please add a --.-- after "securing member"

Column 2, line 67: Please add a --.-- after "clip component" and before "The arms"

Column 3, line 9: Please add a --.-- after "second arm" and before "The second"

Column 4, line 48: Please add a --.-- after "165,167"

Column 4, line 50: Please add a --.-- after "or manually"

Column 5, line 12: Please add a --.-- after "and vessels"

Column 5, line 64: Please add a --.-- after "staple-clip"

Column 6, line 37: Please add a --.-- after "body tissue"

Column 6, line 50: Please add a --.-- after "and 510"

Column 7, line 12: Please add a --.-- after "12(a)-12(d)"

Column 7, line 22: Please add a --.-- after "or vessel"

Column 8, line 19: Please add a --.-- after "or trocar"

Column 8, line 33: Please add a --.-- after "vessel 905"

Column 8, line 48: Please add a --.-- after "one-piece construction"

Column 8, line 58: Please add a --.-- after "end 965"

Column 9, line 17: Please add a --.-- after "safely removed"

Signed and Sealed this
Twenty-eighth Day of June, 2016

Michelle K. Lee
*Director of the United States Patent and Trademark Office*